US006567678B1

(12) United States Patent
Oosta et al.

(10) Patent No.: US 6,567,678 B1
(45) Date of Patent: May 20, 2003

(54) MULTIPLEX SENSOR AND METHOD OF USE

(75) Inventors: Gary M. Oosta, Gurnee, IL (US); Tayy-Wen Jeng, Vernon Hills, IL (US); John M. Lindberg, Grayslake, IL (US); Michael L. McGlashen, Grayslake, IL (US); Joseph L. Pezzaniti, Round Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/571,095

(22) Filed: May 15, 2000

Related U.S. Application Data

(62) Division of application No. 08/982,839, filed on Dec. 2, 1997, now Pat. No. 6,070,093.

(51) Int. Cl.⁷ ................. A61B 5/00; G01J 4/00
(52) U.S. Cl. .............. 600/316; 600/310; 356/364
(58) Field of Search ................. 600/310, 318, 600/319, 320, 316, 322, 328; 356/364, 369, 370

(56) References Cited

U.S. PATENT DOCUMENTS

| 4,655,225 A | 4/1987 | Dahne et al. |
| 4,882,492 A | 11/1989 | Schlager |
| 5,086,229 A | 2/1992 | Rosenthal et al. |
| 5,115,133 A | 5/1992 | Knudson |
| 5,203,328 A | 4/1993 | Samuels et al. |
| 5,209,231 A | 5/1993 | Cote et al. |
| 5,218,207 A | 6/1993 | Rosenthal |
| 5,237,178 A | 8/1993 | Rosenthal et al. |
| 5,313,941 A | 5/1994 | Braig et al. |
| 5,321,265 A | 6/1994 | Block |

(List continued on next page.)

FOREIGN PATENT DOCUMENTS

| DE | 4242083 | 6/1994 |
| WO | 86/07148 | 12/1986 |
| WO | 9210131 | 6/1992 |
| WO | 9307801 | 4/1993 |
| WO | 9402837 | 2/1994 |
| WO | 9405984 | 3/1994 |
| WO | 9413199 | 6/1994 |
| WO | 9639922 | 12/1996 |
| WO | 9728438 | 8/1997 |
| WO | 9734521 | 9/1997 |

OTHER PUBLICATIONS

F.S. LaBella, et al., "Structure of Collagen from Human Tendon as Influenced by Age and Sex", *J. Gerontol.*, vol. 20, pp. 54–59 (1964).

K.M. Quan, et al., "Glucose determination by a pulsed photoacoustic technique: an experimental study using a gelatin–based tissue phantom", *Phys. Med. Biol*, vol. 38, pp. 1911–1922 (1993).

(List continued on next page.)

*Primary Examiner*—Eric F. Winakur
(74) *Attorney, Agent, or Firm*—David L. Weinstein

(57) ABSTRACT

A method for using a multiplex sensor that provides enhanced selectivity and sensitivity. In this method, one or more parameters of a sample are measured by means of multiple spectroscopic techniques, and interferences from physiological and spectral variables are reduced or eliminated. One or more parameters of the sample are measured by means of at least two spectroscopic techniques, wherein the at least two different spectroscopic techniques are selected from the group consisting of:

(a) infrared absorbance
(b) scattering
(c) emission
(d) polarization, and
(e) photoacoustics.

2 Claims, 8 Drawing Sheets

U.S. PATENT DOCUMENTS

| | | |
|---|---|---|
| 5,324,979 A | 6/1994 | Rosenthal |
| 5,337,745 A | 8/1994 | Benaron |
| 5,341,805 A | 8/1994 | Stavridi et al. |
| 5,348,002 A | 9/1994 | Caro |
| 5,348,003 A | 9/1994 | Caro |
| 5,357,960 A * | 10/1994 | Schmidtke et al. ......... 600/310 |
| 5,361,758 A | 11/1994 | Hall et al. |
| 5,362,966 A | 11/1994 | Rosenthal et al. |
| 5,383,452 A | 1/1995 | Buchert |
| 5,435,309 A | 7/1995 | Thomas et al. |
| 5,452,716 A | 9/1995 | Clift |
| 5,481,113 A | 1/1996 | Dou et al. |
| 5,497,769 A | 3/1996 | Gratton et al. |
| 5,515,847 A | 5/1996 | Braig et al. |
| 5,533,509 A | 7/1996 | Koashi et al. |
| 5,553,616 A | 9/1996 | Ham et al. |
| 5,582,168 A | 12/1996 | Samuels et al. |
| 5,626,134 A | 5/1997 | Zuckerman |
| 5,628,310 A | 5/1997 | Rao et al. |
| 5,687,721 A | 11/1997 | Kuhls ......................... 600/316 |
| 5,788,632 A * | 8/1998 | Pezzaniti et al. ........... 600/316 |
| 5,956,144 A * | 9/1999 | Kaplan et al. .............. 600/310 |
| 6,166,807 A * | 12/2000 | Kawamura et al. ......... 356/364 |
| 6,246,893 B1 * | 6/2001 | Gobeli ....................... 600/318 |

OTHER PUBLICATIONS

S.L. Schnider, et al., "Effects of Age and Diabetes Mellitus on the Solubility and Nonenzymatic Glucosylation of Human Skin Collagen", *J. Clin. Invest.*, vol. 67, pp. 1630–1635 (1981).

J.M. Snowden, et al., "Fitreous Structure. VI Age–Related Changes in the Termal Stability and Crosslinks of Vitreous, Articular Cartilage and Tendon Collagens", *Biochimica et Biophysica Acta*, vol. 706, pp. 153–157 (1982).

G.S. Wilson, et al., "Progress toward the Development of an Implantable Sensor for Glucose", *Clin. Chem.*, vol. 38, pp. 1613–1617 (1992).

* cited by examiner

MULTIPLEX SENSOR AND METHOD OF USE

This application is a division of U.S. Ser. No. 08/982,839, filed Dec. 2, 1997, now U.S. Patent No. 6,070,093.

BACKGROUND OF THE INVENTION

1. Field of the Invention

The present invention relates to devices and methods for measuring the concentration of one or more analytes in a biological sample. More specifically, this invention relates to devices and methods for the noninvasive determination of analyte concentrations in vivo, e. g., glucose concentrations in blood.

2. Discussion of the Art

Diabetes: Incidence, Effects and Treatment

Diabetes mellitus is a chronic disorder of carbohydrate, fat, and protein metabolism characterized by an absolute or relative insulin deficiency, hyperglycemia, and glycosuria. At least two major variants of the disease have been identified. "Type I" accounts for about 10% of diabetics and is characterized by a severe insulin deficiency resulting from a loss of insulin-secreting beta cells in the pancreas. The remainder of diabetic patients suffer from "Type II", which is characterized by an impaired insulin response in the peripheral tissues (Robbins, S. L. et al., *Pathologic Basis of Disease*, 3rd Edition, W. B. Saunders Company, Philadelphia, 1984, p. 972). If uncontrolled, diabetes can result in a variety of adverse clinical manifestations, including retinopathy, atherosclerosis, microangiopathy, nephropathy, and neuropathy. In its advanced stages, diabetes can cause blindness, coma, and ultimately death.

The principal treatment for Type I diabetes is periodic insulin injection. Appropriate insulin administration can prevent, and even reverse, some of the adverse clinical outcomes for Type I diabetics. Frequent adjustments of the blood glucose level can be achieved either by discrete injections or, in severe cases, via an implanted insulin pump or artificial pancreas. The amount and frequency of insulin administration is determined by frequent or, preferably, continuous testing of the blood glucose level.

Tight control of blood glucose in the "normal range", 60–120 mg/dL, is necessary for diabetics to avoid or reduce complications resulting from hypoglycemia and hyperglycemia. To achieve this level of control, the American Diabetes Association recommends that diabetics test their blood glucose 5 times per day. Thus, there is a need for accurate and frequent or, preferably, continuous glucose monitoring to combat the effects of diabetes.

Invasive Glucose Measurement

Conventional blood glucose measurements in a hospital or physician's office rely on the withdrawal of a 5–10 ml blood sample for analysis. This method is slow and painful and cannot be used for continuous glucose monitoring. An additional problem for hospitals and physician offices is the disposal of testing elements that are contaminated by blood.

Implantable biosensors have also been proposed for glucose measurement. (G. S. Wilson, Y. Zhang, G. Reach, D. Moatti-Sirat, V. Poitout, D. R. Thevenot, F. Lemonnier, and J.-C. Klein, Clin. Chem. 38, 1613 (1992)). Biosensors are electrochemical devices with enzymes immobilized at the surface of an electrochemical transducer.

Minimally Invasive Glucose Measurement

Portable, "minimally-invasive" testing systems are now commercially available. These systems require the patient to stick themselves to obtain a drop of blood which is then applied to a disposable test strip containing coated reagents or an electrochemical test element.

Although the portable instruments that read the strips are relatively inexpensive ($100–$200), the cumulative cost to diabetics for the disposable strips is considerable. Compliance is another major problem for minimally invasive techniques. Frequent finger sticks are painful and can result in infections, scarring, and nerve damage in the finger. Disposal of potentially biohazardous test strips is yet another problem with this method.

Noninvasive Glucose Measurement

"Noninvasive" (NI) glucose sensing techniques measure in-vivo glucose concentrations without collecting a blood sample. As defined herein, a "noninvasive" apparatus or method is one which can be used without removing a sample from, or without inserting any instrumentation into, the tissues. The concept involves irradiating a vascular region of the body with electromagnetic radiation and measuring the spectral information that results from one of four primary processes: reflection, absorption, scattering, or emission. The extent to which each of these processes occurs is dependent upon a variety of factors, including the wavelength and polarization state of the incident radiation and the glucose concentration in the body part. Glucose concentrations are determined from the spectral information by comparing the measured spectra to a calibration curve or by reference to a physical model of the tissue under examination. A brief description of noninvasive glucose measurements in the prior art is provided below.

Description of the Art

Infrared

NI techniques that utilize the absorption of infrared radiation can be divided into three distinct wavelength regimes: Near-infrared (NIR), Mid-infrared (MIR) and Far-infrared (FIR). As defined herein, NIR involves the wavelength range of from about 600 nm to about 1200 nm, MIR involves the wavelength range of from about 1200 nm to about 3000 nm, and FIR involves the wavelength range of from about 3000 nm to about 25000 nm. As defined herein, "Infrared" (or IR) is taken to mean a range of wavelengths from about 600 nm to about 25000 nm.

NIR

U.S. Pat. Nos. 5,086,229, 5,324,979, 5,237,178 describe a number of noninvasive NIR instruments and methods for measuring blood glucose. In general, a blood-containing body part (e. g., a finger) is illuminated by one or more light sources and the light that is transmitted through the body part is detected by one or more detectors. A glucose level is derived from a comparison to reference spectra for glucose and background interferants.

MIR

The use of MIR radiation for NI glucose measurement has been described in U.S. Pat. Nos. 5,362,966, 5,237,178, 5,533,509, 4,655,225. The principles of operation are similar to those described for the NIR, except that the penetration depth of the MIR light is less than that for NIR. As a consequence, most measurements in this region have been performed using a backscattering geometry. As defined herein, a "backscattering geometry" describes a configuration wherein scattered radiation is collected on the same side of the sample as the entry point of the incident radiation. A "transmission geometry" describes a configuration wherein light is transmitted through the sample and collected on the opposite side of the sample as the entry point of the incident radiation.

FIR

FIR measurements have been described in U.S. Pat. Nos. 5,313,941, 5,115,133, 5,481,113, 5,452,716, 5,515,847, 5,348,003, and DE 4242083.

Photoacoustic Spectroscopy

As will be described more thoroughly below, the photoacoustic (PA) effect results from the absorption of a pulse of optical energy, which is rapidly converted into thermal energy. The subsequent thermal expansion generates an acoustic pressure wave, which is measured by an acoustic transducer. In addition to the absorption of light, the measured PA signal depends upon the speed of sound in the medium, the thermal expansion coefficient of the analyte, and the specific heat of the medium.

Glucose measurements employing the photoacoustic effect have been described by Quan et al. (K. M. Quan, G. B. Christison, H. A. MacKenzie, P. Hodgson, Phys. Med. Biol., 38 (1993), pp. 1911–1922) and U.S. Pat. No. 5,348, 002.

Caro et al. (U.S. Pat. No. 5,348,002) provides a PA detector and an optical detector; however, the device and method of Caro require that a relationship be drawn between the "photoacoustic response and the degree of absorption" of the sample. As will be described more fully below, the present invention requires no such a priori information. Rather, it is based solely upon a correlation between the measured PA signal and the analyte concentration. Further, the present invention employs focusing optics in order to generate a more concentrated PA signal than the apparatus of Caro et al., which employs the diverging output of an optical fiber for photoexcitation. As a result, the present invention is more sensitive and more efficient in its operation than are the device and method of Caro.

Scattering

As defined herein "scattering" includes Rayleigh, Mie, and Raman scattering. Glucose decreases the intensity of Mie scattering by decreasing the refractive index difference between the extracellular fluid (ECF) and cell membranes. Gratton et al. (U.S. Pat. No. 5,497,769) have proposed a sensor based upon this effect; however, the signal to noise ratio for this technique is expected to be inadequate for glucose measurement.

Raman Scattering

U.S. Pat. No. 5,553,616 teaches the use of Raman scattering with excitation in the near infrared (780 nm) and an artificial neural network for measuring blood glucose. Glucose Raman bands that are distinct from protein Raman bands may be chosen, however, the sensitivity of this method limits its applicability for in-vivo measurements. WO 92/10131 discusses the application of stimulated Raman spectroscopy for detecting the presence of glucose.

Polarimetry

Methods for the determination of glucose concentrations using changes in the polarization of light are described in International Patent Publications WO 92/10131, WO 93/07801, WO 94/02837, WO 94/05984, and WO 94/13199 and U.S. Pat. Nos. 4,882,492, 5,086,229, 5,209,231, 5,218, 207, 5,321,265, 5,337,745, 5,361,758, and 5,383,452.

Emission

As used herein, "emission" measurements are defined as measurements of fluorescence or phosphorescence. Emission spectroscopic measurements have been described in U.S. Pat. Nos. 5,341,805, 5,383,452, 5,626,134 and 5,628, 310, and 5,582,168.

Challenges for NI Glucose Measurement

The NI techniques listed above are painless, reagentless, and are less expensive than the finger stick approach over the life of the patient. NI testing also eliminates the potentially biohazardous waste associated with invasive and minimally invasive measurements. However, NI methods have not yet achieved the level of accuracy and precision that is required for measuring physiologically relevant glucose concentrations in-vivo.

A major challenge for all of the noninvasive techniques to date has been to collect spectral information with sufficiently high signal-to-noise ratios to discriminate weak glucose signals from the underlying noise. In the ideal case, a noninvasive sensor would be highly sensitive for the parameter of interest (e. g., glucose concentration) while remaining insensitive to interfering analytes or physiological parameters. In practice, all of the noninvasive measurement techniques described in the prior art are sensitive to one or more interfering "physiological" or "spectral" variables.

Physiological and Spectral Variables

As used herein, the term "physiological variables" describes physiological parameters, such as temperature or pulsatile blood flow, that can adversely affect the sensitivity or selectivity of a noninvasive measurement. Examples of several important physiological variables are listed in Table 1 below. As used herein, the term "spectral variables" describes spectral features that arise either from poorly resolved analyte bands or from other interfering components in the sample. Several significant sources of spectral interference in biological samples such as water, hemoglobin, albumin, cholesterol, urea, and fat are listed in Table 2 below. Other tissue constituents that are present at lower concentrations or have lower absorption cross-sections may also contribute to an overall background signal that is difficult to subtract.

TABLE 1

| | Char. Frequ. (Hz)[a] | Vis. Raman[b] | NIRRaman[b] | Fluorescence[b] | NIR[b] | MIR[b] | Polarization[b] | Photoacoustics[b] |
|---|---|---|---|---|---|---|---|---|
| Subject Temperature | 0.1–1 | 6 | 6 | 5 | 2 | 2 | 3 | 2 |
| pH | 0.01 | 3 | 3 | 5 | 3 | 3 | 5 | 5 |
| Tissue Scattering | 10–100 | 1 | 3 | 5 | 3 | 3 | 8 | 8 |
| Pulsatile flow | 1 | 5 | 5 | 5 | 7 | 4 | 8 | 8 |
| Body part movement | 1–10 | 2 | 4 | 4 | 1 | 1 | 3 | 3 |
| Electrolyte Concentrations | 0.1–1 | 3 | 3 | 5 | 3 | 3 | 8 | 4 |
| Pressure at the interface | .1–10 | 6 | 6 | 3 | 3 | 3 | 5 | 3 |
| Refractive Index | 0.1–10 | 5 | 4 | 3 | 3 | 3 | 5 | 3 |

Legend
[a]Numerals in this column indicate the oscillation frequencies (Hz) of several important physiological variables.
[b]Numerals in this column indicate the relative sensitivity (1–10, 1 being most sensitive) of the spectroscopic measurement to several important physiological variables.

TABLE 2

|  | Char. Frequ. (Hz) | Vis. Raman | NIRRaman | Fluorescence | NIR | MIR | Polarization | Photoacoustics |
|---|---|---|---|---|---|---|---|---|
| Water | 0.1–0.01 | 10 | 10 | 10 | 1 | 1 | 8 | 6 |
| Hemoglobin | 1 | 1 | 2 | 2 | 2 | 2 | 6 | 7 |
| Albumin | 0.1–0.01 | 5 | 5 | 2 | 3 | 2 | 3 | 7 |
| Cholesterol | 0.01–0.001 | 7 | 7 | 9 | 4 | 3 | 1 | ? |
| Urea | 0.1 | 5 | 5 | ? | 2 | 2 | 5 | ? |
| Fat | 0.1 | ? | ? | 10 | 2 | 2 | 5 | ? |
| General "Background" | 10–100 | 1 | 3 | 2 | 3 | 3 | 5 | ? |

Legend
[a]Numerals in this column indicate the oscillation frequencies (Hz) of several important spectral variables.
[b]Numerals in this column indicate the relative sensitivity (1–10, 1 being most sensitive) of the spectroscopic measurement to several important spectral variables.

Physiological and spectral variables can introduce unwanted noise, or worse, completely overwhelm the measured signals of interest (e. g., those related to glucose concentration). It is difficult to eliminate these interferences because they may exhibit one or more of the following properties:

(a) they may contribute nonlinearly to the measured signal,
(b) they may vary with spatial location within the sample,
(c) they may vary over time, or
(d) they may vary from sample to sample.

Examples of (a) nonlinear, (b) spatial, (c) temporal, and (d) sample-dependent interferences are briefly described below.

(a) Nonlinear Contributions

A change in temperature can have a nonlinear effect on the infrared spectrum by altering the intensities as well as the frequencies of the dominant water absorption bands. A temperature change will also modify the refractive index of the sample which, in turn, will alter the scattering properties of the sample. The effective optical path length will change as a result of the aforementioned change in scattering properties. Thus, physiological and spectral parameters are often inseparably linked and a change in one of these variables can modulate the impact of other interfering variables. The result is a nonlinear change in the measured signal for a linear change in one of the physiological or spectral variables.

(b) Inhomogeneous Distributions

Physiological or spectral variables can also vary over one or more spatial dimensions of the sample. Human skin, for example, is an important obstacle for noninvasive measurements because of its multilayered, three-dimensional architecture. Human skin comprises the stratum corneum, the epidermis, and the dermis. Biological chromophores (spectral variables) may be confined to a single layer or may be evenly distributed among multiple layers. Melanin, for example, is distributed between the epidermis and stratum corneum, whereas the various forms of hemoglobin are confined to vessels of the dermis, and only indirectly exert any influence on the optical properties of the overlying epidermis.

(c) Time Varying Contributions

Referring again to Tables 1 and 2, each of the physiological and spectral variables may fluctuate over time and each variable may oscillate at a different frequency. Although the mechanisms governing the modulation of the spectral and physiological variables listed in Tables 1 and 2 are not yet fully understood, the frequencies of oscillation are predictable, or at least measurable. A few representative examples are described below.

Tissue perfusion (and consequently tissue temperature) can fluctuate for a variety of reasons, including local infections, inflammation, and some malignancies. A familiar example is the change in skin coloration, which can accompany exercise, alcohol intake, or even a change in position from sitting to standing.

On a longer time scale, the physical properties of human skin change as a normal function of aging. These changes include decreased solubility (Schnider, S. L., and Kohn, R. R., J. Clin. Invest. 67, (1981) pp.1630–1635), decreased proteolytic digestibility (Hamlin, C. R., Luschin, J. H., and Kohn, R. R., Exp. Gerontol. 13, (1978) pp. 415–523), increased heat denaturation time (Snowden, J. M., Eyre, D. R., and Swann, D. H., Biochem. Biophys. Acta, 706, (1982) pp. 153–157), and the accumulation of yellow and fluorescent materials (LaBella, F. S., and Paul, G., J. Gerontol., 20, (1964) pp. 54–59). These changes appear to be accelerated in diabetes, and may alter the scattering properties of the skin via the formation of intermolecular crosslinks between collagen fibrils.

(d) Sample to Sample Variability

The influence of physiological and spectral variables may differ from individual to individual or between measurements, thereby leading to irreproducible results. As mentioned previously, individual differences in the optical properties of skin such as those due to aging or race (melanin content) can dramatically affect noninvasive measurements.

Signal Processing

In an attempt to selectively extract glucose-dependent information in the presence of dominating signals from the physiological and spectral variables described above, skilled artisans in the field have applied a variety of sophisticated mathematical algorithms. These have included principal components regression (PCR), partial least squares (PLS), and artificial neural networks (ANN), among others. The results of signal processing, however, are highly dependent upon the quality of the starting data. PLS and ANN algorithms are powerful techniques for correlating minute spectral variations with analyte concentration. However, these methods are also sensitive to time-varying fluctuations in physiological and spectral variables that happen to correlate with changes in analyte concentration. Without adequate compensation for the effects of physiological and spectral variables, PLS and ANN algorithms can highlight such correlations and provide misleading results.

State of the Art

Thus, despite the variety of spectroscopic techniques employed and the advanced signal processing algorithms used for data manipulation, there is still no commercially available device that provides noninvasive glucose measurements with a sensitivity that is comparable to the invasive methods. All of the prior art methods respond to glucose concentrations, but they are also sensitive to physiological and spectral variables. As a result, current approaches to non-invasive glucose testing have not achieved acceptable precision and accuracy.

Thus, there is a continuing need for improved noninvasive analytical instruments and methods that will provide essentially the same accuracy as conventional, invasive blood glucose tests. There is also a need for noninvasive, low-cost methods and instruments for the measurement of glucose levels in diabetic or hypoglycemic patients. There is also a need for a durable, cost-effective, reagent-free, painless, and environmentally friendly apparatus for measuring blood glucose.

SUMMARY OF THE INVENTION

The present invention solves a fundamental problem that has plagued noninvasive measurements in the prior art. Namely, for any given noninvasive measurement performed on a biological sample, multiple physiological and spectral variables can interfere with the measurement of the parameter(s) of interest (e. g., the concentration of an analyte, such as glucose). As described above, physiological and spectral interferences are difficult to remove because they can exhibit any or all of the following properties:

(a) they may contribute nonlinearly to the measured signal, (b) they may vary with spatial location within the sample, (c) they may vary over time, or (d) they may vary from sample to sample.

As will be described more fully below, the present invention measures the reflected, scattered, absorbed, emitted, or transmitted light as a function of multiple dimensions. As defined herein, a "dimension" is a measured quantity. It can be related to light which is reflected, scattered, absorbed, emitted, or transmitted by the sample. It can also be related to time or space or both.

For example, a spectral dimension might comprise the wavelength of light absorbed by the sample, the polarization state of light entering or exiting the sample, the angle of incidence of light entering or exiting the sample, a difference between the frequencies (or wavelengths) of light entering and exiting the sample, a difference between the polarization states of light entering and exiting the sample, the angle between the light entering and exiting the sample, or some other observable spectral property.

A temporal dimension might include, for example, the duration of time between the entry of light into the sample and the exit of light from the sample, the duration of time between the entry of light into the sample and the detection of a measured spectroscopic signal (e. g., acoustic energy), the duration of time between spectroscopic measurements, an oscillation frequency of the sample, an oscillation frequency of the spectroscopic measurement or some other variable which is measurable in the time or frequency domain.

A spatial dimension might include, for example, a distance along one or more Cartesian or polar coordinates such as a separation distance between two or more points in the sample, the size of a constituent of the sample (e. g., a particle size), the distance or angle between a detector and the sample, the effective optical path length in the sample, or a spatial frequency of the sample.

In the present invention, physiological and spectral interferences are measured over multiple dimensions so that their contributions may be separated, quantified, and removed from the signals of interest (e. g., those related to the concentration of an analyte, such as glucose). A multivariate algorithm is employed to selectively extract parameters of interest from the measured signals.

In one embodiment, the present invention comprises a multiplex sensor and a method of use that provides enhanced selectivity and sensitivity. In this method, one or more parameters of the sample are measured by means of multiple spectroscopic techniques, and the interferences from physiological and spectral variables are reduced or eliminated.

Another embodiment of the present invention comprises a multiplex sensor and a method of use that provides enhanced selectivity and sensitivity. One or more parameters of the sample are measured by means of at least two different spectroscopic techniques, wherein the at least two different spectroscopic techniques are selected from the group consisting of:

(a) infrared absorbance
(b) scattering
(c) emission
(d) polarization, and
(e) photoacoustics Weaknesses or interferences present in the measurements from one spectroscopic technique are compensated by a different technique.

Another embodiment of the present invention comprises an apparatus and method for measuring one or more parameters of a sample (e. g., the presence or concentration of one or more analytes) by means of at least two spectroscopic techniques selected from different members of the group consisting of:

(a) infrared absorbance
(b) scattering
(c) emission
(d) polarization, and
(e) photoacoustics wherein the measurements are recorded as a function of at least one spatial dimension.

Another embodiment of the present invention comprises an apparatus and method for measuring one or more parameters of a sample (e. g., the presence or concentration of one or more analytes) by means of at least two spectroscopic techniques selected from different members of the group consisting of:

(a) infrared absorbance
(b) scattering
(c) emission
(d) polarization, and
(e) photoacoustics wherein the measurements are recorded as a function of at least one temporal dimension.

Another embodiment of the present invention comprises an apparatus and method for measuring one or more parameters of a sample (e. g., the presence or concentration of one or more analytes) by means of at least two spectroscopic techniques selected from different members of the group consisting of:

(a) infrared absorbance
(b) scattering
(c) emission
(d) polarization, and
(e) photoacoustics wherein the measurements are recorded as a function of at least one spatial dimension and at least one temporal dimension.

Another embodiment of the present invention provides enhanced selectivity by illuminating the sample with electromagnetic radiation and recording the intensity of the reflected, absorbed, scattered, emitted or transmitted radiation as a function of at least three dimensions wherein the at least three dimensions are selected from the group consisting of:

(a) spectral dimensions, (b) temporal dimensions, and (c) spatial dimensions.

and wherein at least two of the at least three dimensions are spectral dimensions. Preferably, at least three of the at least three dimensions are spectral dimensions.

Another embodiment of the present invention comprises an apparatus and method for making multiple, consecutive measurements of at least one parameter of a sample (e. g., the presence or concentration of one or more analytes) by means of at least two spectroscopic techniques selected from different members of the group consisting of:

(a) infrared absorbance (b) scattering (c) emission (d) polarization (e) photoacoustics Another embodiment of the present invention comprises a multiplex sensor and a method of use that provides enhanced selectivity and sensitivity. One or more parameters of the sample are measured by means of at least three different spectroscopic techniques, wherein said at least three different spectroscopic techniques are selected from the group consisting of:

(a) infrared absorbance (b) scattering (c) emission (d) polarization, and (e) photoacoustics In another embodiment, an improved apparatus and method are provided for measuring the presence or concentration of one or more analytes (e. g., glucose, alcohol, blood urea nitrogen, bilirubin, hemoglobin, creatine, electrolytes, blood gases, cholesterol, hormones or drugs of abuse) in a sample.

The present invention is particularly advantageous for biological samples where multiple interfering analytes or physiological variables can affect the measurement. The sample may be obtained using invasive or minimally invasive means. Alternatively, noninvasive measurements may be made on a body part of a patient, e. g., a finger, earlobe, lip, toe, skin fold, or bridge of the nose.

DETAILED DESCRIPTION

Figure 1A:
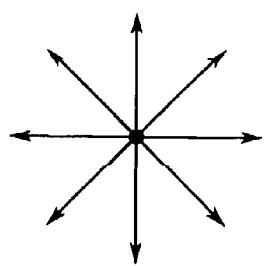
FIG. 1 is a schematic diagram of the polarization properties of light.

In order to fully appreciate the advantages of the present invention it is helpful to review the underlying operating principles of the spectroscopic techniques employed herein. A discussion of several preferred spectroscopic measurements is provided below along with a description of important physiological and spectral variables and their effects on these measurements. A description of compensation for physiological and spectral variables is also provided and several preferred embodiments are described.

The Multiplex Approach

When electromagnetic radiation impinges on a sample, the radiation is reflected, scattered, absorbed, emitted, or transmitted. The extent to which any of these processes occurs depends upon the chemical constitution of the sample as well as the frequency (or wavelength), polarization state, and angle of incidence of the impinging light beam. The methods of the prior art employ only a small fraction of the available spectroscopic information for measurement purposes. As a result, they are unable to accurately measure glucose in the presence of dominating contributions from physiological and spectral interferences.

Biological samples are notoriously complex, and the present invention provides multiple dimensions of information in order to sort out the components of the spectroscopic signal that arise from glucose in the presence of large background signals. The discussion provided below describes several spectroscopic techniques that are preferred for performing noninvasive measurements in the present invention.

Infrared Absorbance

Infrared absorptions result from the vibrational and rotational oscillations of the constituents of the sample. Because water is the main constituent of biomedical samples, its optical properties (in particular its absorption coefficient) determine the applicability of IR spectroscopy for noninvasive measurements.

The NIR region of the electromagnetic spectrum is generally considered to be the most useful region for in-vivo diagnostic applications because living tissue is largely transparent in this region. Absorption bands in the NIR region result primarily from the combination of overtone bands of the fundamental vibrational modes. Consequently, these bands are very weak in intensity, typically less than one tenth of the intensity of the fundamental vibrational modes.

Nearly all chemical species exhibit absorption bands in this interval, thereby making selectivity a problem for NIR measurements. Because NIR radiation is capable of penetrating several centimeters of body tissue, NIR spectra contain signals from constituents of the blood, interstitial fluid, and skin. NIR is very accurate for the measurement of hemoglobin, total protein, HDL, and triglycerides; however, measurements of glucose that rely on NIR spectra alone have not achieved an acceptable level of precision and accuracy. In the present invention, the combination of NIR measurements with complementary spectral data yield a more accurate measure of glucose concentration.

MIR spectral analysis is difficult for non-invasive blood glucose measurement as the absorption at these wavelengths in the human skin is very large. The glucose MIR spectrum is dominated by the water absorptions; however, this spectral range provides higher molecular selectivity than does the NIR spectrum. MIR is insensitive to hemoglobin absorption in its oxy- and deoxy- forms. It is also insensitive to urea, bilirubin, and other major blood constituents.

Photoacoustic Spectroscopy

Pulsed photoacoustic spectroscopy (PAS) employs pulses of light, preferably from a laser, at a wavelength chosen to interact with the analyte. For noninvasive measurements, the laser pulses are fired into the tissue and the light is absorbed by the analyte, thereby generating microscopic local heating and a rapid rise in temperature. The temperature rise generates an ultrasound pressure wave, which is detectable on the surface of the skin. Conversion of the pulse of optical energy into acoustic energy is based on the radiationless relaxation of absorbed light energy into thermal energy. The subsequent thermal expansion generates an acoustic pressure wave. The magnitude of the pressure, IPI, is proportional to:

$$\frac{\varepsilon \beta v^n}{C_p}$$

where $\varepsilon$ is the optical extinction coefficient, $\beta$ is the thermal expansion coefficient, $v$ is the velocity of sound in the sample, $C_p$ is the specific heat of the sample and n is an exponent that can range between (0.5–2.0). In solution, the photoacoustic response is similar to the infrared spectrum. However, there are two major differences for tissue measurements:

(a) First, the optical absorption is multiplied by a factor that is dependent upon the speed of sound and the specific heat of the. medium. At an optical wavelength that is absorbed by the analyte, the change in the PAS signal due to an analyte concentration change is composed of contributions from both the optical absorption change, $\Delta \varepsilon$, and the physiological parameter change $$\Delta\left(\frac{\beta v^n}{C_p}\right)$$

(b) Secondly, the photoacoustic response is a function of the optical energy absorbed (as opposed to transmitted). Thus, scattering effects are much less important for PAS measurements than for optical absorbance measurements.

Photoacoustic measurements are highly sensitive to blood glucose concentrations and are less sensitive to water than other infrared measurements, due to the high specific heat of water. In addition, photoacoustic measurements may be performed using IR wavelengths that are longer than the performance range of typical IR absorbance detectors. Spectral interferants for in vivo photoacoustic measurements have not been well characterized.

Scattering

An electromagnetic wave incident on an isolated molecule will cause the electrons to oscillate about their equilibrium positions, in synchrony with the applied wave. The resulting electronic oscillator emits radiation (scatters) in all directions in a plane perpendicular to the oscillating electrons. Some molecules are more susceptible to applied electromagnetic waves than others, and the tendency of their electrons to oscillate is defined by a parameter, $\alpha$, called the polarizability.

Refraction is the result of radiation scattered in the same direction as that of the incident light wave. The phase of the scattered wave is different from that of the wave that passes through the sample. These two types of waves then recombine (interfere) to produce a wave that has apparently passed through the sample with a different velocity. The parameter used to describe this phenomenon is called the refractive index (n) defined as:

$$n=(C_o/C_s)$$

where $C_o$ is the velocity of light in a vacuum and $C_s$ is the velocity of light in the sample.

The refractive index, and therefore the scattering, is dependent on frequency. Frequency-dependent refraction is known as dispersion, the phenomenon that gives rise to the familiar splitting of white light into colors by a prism. The frequency dependence of scattering, and therefore n, depends on $\alpha$, the wavelength ($\lambda$), the polarization state, and the number and size of the scatterers. For particles that are small with respect to the wavelength (Rayleigh scattering), scattering scales as $1/\lambda^4$. For tissue samples where the size of the scatterers (cells) is near the wavelength of light (Mie scattering), the scattering intensity scales approximately as $1/\lambda^{3/2}$.

In tissues, light scattering occurs because of a mismatch between the index of refraction of the ECF and the cells and organelles comprising the tissue. The index of refraction of the ECF varies as its composition changes, whereas the index of the cellular membranes and organelles remains relatively constant.

A change in the glucose concentration in tissues can alter the intensity and directionality of scattering; however, a direct measurement of glucose via scattering is difficult because:

(a) the change in scattering produced by a physiologically relevant change in glucose concentration is extremely weak, (b) a change in glucose concentration can initiate a complex interplay of hormonally-regulated metabolic reactions in the intra- and extracellular fluid, the products of which reactions may also alter scattering intensity, and (c) a change in glucose concentration may also alter the size of the cells (and thus their scattering properties) via a change in osmolarity of the ECF.

Raman Scattering

When light impinges on a sample, most of the scattered photons are elastically (or Rayleigh) scattered, meaning that they have the same frequency as the incident radiation. A small fraction of the scattered light (approximately one in a thousand incident photons) is inelastically scattered at frequencies that are shifted by frequencies defined by molecular vibrations. Raman scattering occurs at frequencies corresponding to the incident frequency plus or minus a molecular vibrational frequency as shown below:

$$v_{Raman}=v_o=v_{vib}$$

where $v_{Raman}$ is the Raman scattered frequency, $v_o$ is the incident (laser) frequency and $v_{vib}$ is a vibrational frequency of the molecule under study. Raman bands having frequencies that are lower than the incident frequency are called "Stokes" shifted bands. Those with frequencies that are higher than the incident frequency are called "Anti-Stokes" bands. Stokes and Anti-Stokes shifted Raman bands are displaced symmetrically about the incident frequency. A Raman spectrum is thus a vibrational spectrum that is obtained by recording the intensity of scattered light as a function of frequency.

Because the selection rules for Raman scattering are different from those of MIR or NIR, Raman scattering is complementary to these other techniques. In other words, vibrational modes that produce intense Raman bands may be invisible in the MIR or NIR spectra. Additionally, some IR and NIR vibrational bands may not be present in the Raman spectrum. Raman spectroscopy has a distinct advantage when compared with infrared measurements in that Raman spectroscopy can be performed easily in water. Further, glucose Raman bands that are distinct from protein Raman bands can be chosen. Unfortunately, the intensity of a "normal" Raman spectrum is usually weak.

If the laser excitation frequency lies within an electronic absorption band of a chromophore in the molecule, then some vibrations associated within that chromophore can be dramatically enhanced. This technique, known as Resonance Raman scattering, can be used to increase the sensitivity of the measurement. For example, NIR excitation into the heme absorption bands will cause an enhancement of the heme vibrational modes, far above the intensity of the protein Raman bands. Normal and Resonance Raman spectroscopies may thus yield vibrational information that is complementary to that obtained by IR or NIR methods.

Polarimetry

Figure 1B:
Figure 1C:
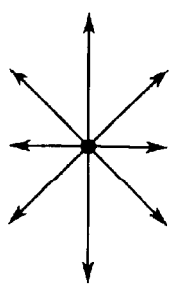
Figure 1D:
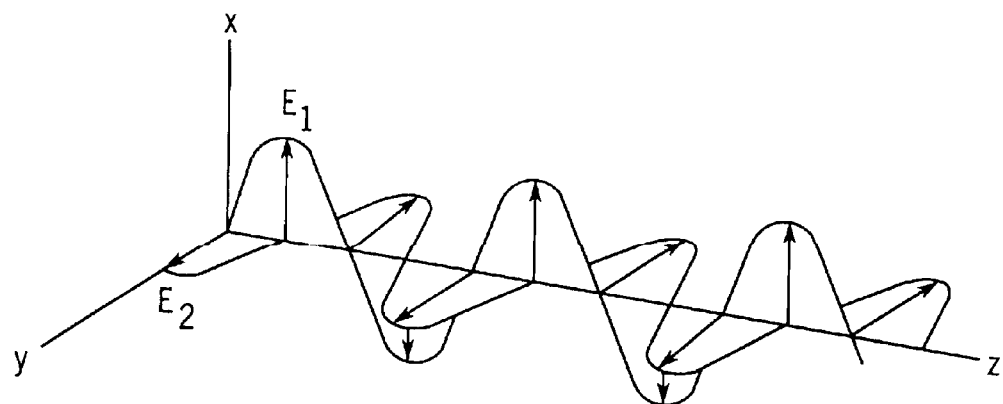
Figure 1E:
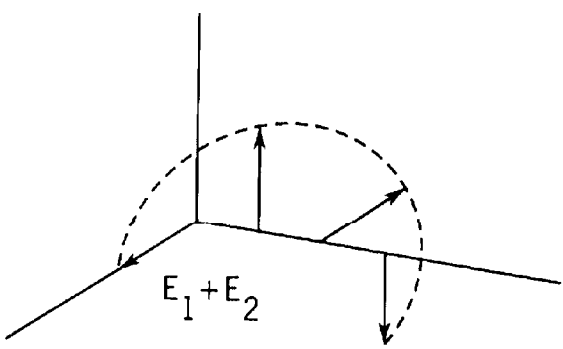

As shown in FIG. 1(a), unpolarized light contains oscillations of the electric (E-) field in all directions perpendicular to the direction of propagation. Plane, or linearly, polarized radiation has oscillations of the E-field in only one plane, as shown in FIG. 1(b). Plane polarized light can be considered to arise from a source that oscillates parallel to the x-axis. If the source also oscillates parallel to the y-axis with the same phase and amplitude, then the two waves superimpose to produce another plane-polarized wave oriented at 45° relative to the x-axis. When the oscillations are not in the same phase, the superposition of the two waves does not lead to a fixed direction for E. For example, if the phase difference is $\pi/2$, as shown in FIG. 1(d–e), then the path of the E-vector is helical. Such light is said to be circularly polarized. Similarly, plane polarized light may be said to arise from the superposition of two equal amounts of mutually coherent beams of right-circularly polarized light and left-circularly polarized light. If the two components of oscillation along the x-axis and the y-axis are unequal in amplitude, then the resultant wave is elliptically polarized. In practice, light is neither completely polarized nor completely unpolarized; both cases are extremes. More often, the electric field is partially polarized. This can be envisioned as the superposition of specific amounts of polarized and unpolarized light.

Chiral molecules, such as glucose, are molecules that cannot be superimposed on their mirror image. A unique property of chiral molecules is that they are optically active, i. e., they have different refractive indexes for Left- and Right-circularly polarized light. Their differential interaction with Left- and Right-circularly polarized light is measured by means of a technique called polarimetry. Polarimetry is a method of measuring and describing changes in the polarization state of light upon interaction with a polarization element (e. g. a sample). The polarization properties of a polarization element can be divided into three groups: (1) diattenuation, (2) retardance, and (3) depolarization (see, for example, J. L. Pezzaniti, Mueller Matrix Imaging Polarimetry, Dissertation, 1993).

Diattenuation refers to the difference in intensity of the transmittance (or reflectance) of the two polarization states with maximum and minimum transmittance (or reflectance). Diattenuation may be described mathematically as:

$$Diattenuation = \frac{I_{max} - I_{min}}{I_{max} + I_{min}}$$

where $I_{max}$ is the intensity of the maximally transmitted (or reflected) polarization state and $I_{min}$ is the intensity of the minimally transmitted (or reflected) polarization state. When D=1, the sample is a polarizer, i.e. only one polarization state exits the sample. When D=0, the sample does not display diattenuation. When 0<D<1, the sample is a diattenuator. A diattenuator may be linear, circular or elliptical.

There are subtle, but important differences between diattenuation and dichroism. Diattenuation is measured as the difference in scattered intensity between two orthogonal polarization states. The orthogonal polarization states might be Left-circularly polarized versus Right-circularly polarized states (for a circular diattenuator) or Vertical-polarized versus Horizontally-polarized states (for a linear diattenuator). In diattenuation, the scattered intensity is modulated by both absorption and scattering processes. This contrasts with dichroism, which measures the difference in the amount of light absorbed by two orthogonal polarization states.

For turbid samples, e. g. biological samples, scattering effects are important and diattenuation measurements are performed. For weakly scattering samples, diattenuation typically reduces to the simpler circular dichroism measurement.

Retardance is the difference in phase accumulation (optical path length) between the two eigenpolarization states of a polarization element (e. g. a sample). An eigenpolarization state is a polarization state that is unchanged by the polarization element except for an overall change in amplitude or phase. For an anisotropic material, retardance is given by $$\delta = 2\pi(n_1 - n_2)\delta/\lambda$$

Where $n_1$ and $n_2$ are the indices of refraction for the two eigenpolarization states, $\delta$ is the thickness of the sample, and $\lambda$ is the wavelength of light. Retardance is most often measured as a difference in the refractive index ($n_L \neq n_R$) for Left-circularly polarized and Right-circularly polarized light. If $n_L \neq n_R$, then the phase accumulation of Left-circularly polarized and Right-circularly polarized beams in the sample will be different, and the resultant vector sum of the Left-circularly polarized and Right-circularly polarized beams will be rotated with respect to the situation in the absence of the sample. This is the phenomenon of optical rotation.

Chiral molecules, such as glucose, display retardance and the concentrations of chiral molecules can be derived from measurements of optical rotation angle. This angle is extremely small for physiologically relevant glucose concentrations, and a number of chiral molecules (e. g. fructose, cholesterol) contribute to the measurement in biomedical samples. Selectivity can be enhanced by measuring the rotation angle as a function of wavelength.

Depolarization is a process in which completely polarized light is coupled to unpolarized light and is defined as $$D = \frac{\text{Polarized Light}}{\text{Total Incident Light}}$$

In turbid media, an incident polarized light beam undergoes multiple scattering events. The polarization of the incident beam is degraded with each scattering event, and the depolarization can be used as a measure of the number of scattering events in the medium. Because glucose influences the overall refractive index in tissue, the number of scattering interactions changes with varying glucose concentrations, because scatter is a strong function of refractive index. As the number of scattering interactions increases, the polarized light becomes increasingly depolarized. Thus as glucose concentration changes, the scatter distribution changes and the depolarization can be monitored as an indirect measurement of scatter and glucose concentration.

Emission

In general, a molecule at room temperature will be in its ground electronic state ($S_o$) and its lowest vibrational energy level. Absorption of an appropriate amount of energy (ultraviolet, visible, and some NIR absorptions) will result in the excitation of the molecule from its $S_o$ state into the upper vibrational levels of a higher electronic energy level, usually the first excited singlet state ($S_1$). In many instances, the excitation energy is lost as heat to the surroundings as the molecule returns (relaxes) to the ground state. However, in some cases, reradiation (emission) occurs. Fluorescence and phosphorescence are two particular kinds of emission known, collectively, as luminescence.

Fluorescence usually occurs at a lower frequency than that of the incident light. This is because the absorption process puts the molecule in an excited vibrational level of the $S_1$ excited state. Rapid decay to the lowest vibrational level of the excited state occurs before emission. The sensitivity for fluorescence measurements is high because the detection frequency is different from the incident frequency and there is no background signal from the excitation source. It is often possible to measure fluorescence from analytes at concentrations in the $10^{-8}$ M range, which is typically two to four orders of magnitude below those generally provided by absorption techniques.

Fluorescence is also a powerful tool for kinetic studies because there are many reactions, solvent rearrangements, and molecular motions that take place on the same time scale as the lifetime of the excited state ($10^{-6}$–$10^{-9}$ seconds). The sensitivity of fluorescence to this time scale provides many applications to biological systems. Fluorescence studies of biological samples can measure the emission from both endogenous (natural) and exogenous (probe) fluorophores. Natural fluorophores include aromatic amino acids, flavins, vitamin A, chlorophyll, and NADH. Several parameters may be measured to provide information about the environment and dynamics of the fluorophor under study. These parameters may be described as follows:

1) $\lambda_{max}$

The dependence of the fluorescence intensity on the wavelength of the exciting light is referred to as the excitation spectrum. Conversely, the fluorescence emission spectrum describes the variation of the fluorescence intensity with the wavelength of the emitted light. The position of the maximum in the emission spectrum ($\lambda_{max}$) is sensitive to the polarity of the environment and the mobility of the fluorophore.

2) Fluorescence lifetime

The lifetime of the molecule in the excited state depends on competition between the radiative emission and any radiationless processes, such as the transfer of the excitation energy to the surrounding medium. These nonradiative processes provide an alternative mechanism for the excited molecules to relax back to the ground state, and their presence results in a diminution (quenching) of the fluorescence intensity. The lifetime can therefore be used to measure the rate constants for both radiative and non-radiative processes.

3) Quantum yield

The quantum yield for fluorescence (the fluorescence efficiency) describes the fraction of molecules in the excited state which are deexcited by fluorescence. The quantum yield is sensitive to the polarity of the environment as well as other quenching processes, such as resonant energy transfer and collisional quenching by solvent molecules.

4) Fluorescence polarization

For a sample of randomly oriented fluorophores excited with plane polarized light, a fraction of the fluorophores will emit fluorescence that is polarized in a direction parallel to the incident radiation and a fraction of the fluorophores will emit fluorescence in a direction perpendicular to the incident radiation. By using a pulsed excitation source and monitoring the intensity of the fluorescence emitted in directions parallel and perpendicular to the incident radiation over time, it is possible to determine rotational time constants of the fluorophores.

All of the fluorescence parameters described above may be used to measure analyte properties (such as concentration or dynamics), however, all of these methods suffer from absorption and scattering interferences in the sample. Absorption and/or scattering by the sample will produce a misleading result that underestimates the intensity of fluorescence emission. Scattering processes will randomize the polarization states of the emitted light. In the present invention, absorption and/or scattering measurements are used to correct the fluorescence measurements and provide a more accurate reading of $\lambda_{max}$, fluorescence lifetime, quantum yield, and fluorescence polarization.

Compensation for Physiological Variables

The combination of two or more spectroscopic techniques selected from those listed above provides an advantage over methods provided in the prior art. By performing measurements using two or more of the noninvasive techniques listed above, it is possible to eliminate noise that results from physiological or spectral variables. In a preferred embodiment, two or more of the spectroscopic techniques listed above are combined substantially simultaneously. As used herein, "substantially simultaneously" is defined as within a time period of from about 0 hours to about 1 hour or, preferably, from about 0 hours to about 0.1 hour or, more preferably, from about 0 to about 1 minute, or even more preferably from about 0 to about 1 second, or most preferably, simultaneously.

Corrections for Tissue Scattering

Light scattering depends on the wavelength and the polarization state of the incident light as well as the difference in refractive index between the scattering center(s) and the surrounding medium. For tissue samples, light scattering arises from the refractive index mismatch between cell or mitochondrial membranes, collagen fibers or other organelles, and the extracellular fluid (ECF) of the tissue. As used herein, tissue scattering is taken to mean light that is scattered by tissues. Tissue scattering can change over temporal or spatial dimensions due to a variety of factors, such as the water distribution or collagen content in the tissues, diet, or disease states, such as diabetes or hypertension. For example, an increase of water in the tissue ECF will decrease the index of refraction, thereby increasing the difference in refractive index between the ECF and the cell membranes, thereby increasing tissue scattering. Tissue scattering can vary considerably between individuals due to changes in skin properties, disease states, diet or even exercise.

Tissue scattering can lead to spurious or nonlinear results for spectroscopic measurements for a variety of reasons. First, scattering results in a loss of transmitted intensity due to scattering at angles that are outside the numerical aperture of the collection optics. For an absorbance measurement, the effect is a misleading reading that overestimates the amount of light absorbed. Secondly, multiple scatter events within the tissue lead to an ill-defined optical path length. Photon trajectories through the tissue are not rectilinear as they are in homogenous media. Multiple reflections and refractions effectively increase the optical path length.

The polarization measurements described above can be used to compensate for (normalize) the effects of scattering on spectroscopic measurements. Diattenuation, retardance, and depolarization measurements provide a complete description of the polarization properties, and therefore the refractive index, of the sample. In particular, depolarization may be used as a measure of person-to-person or day-to-day variation in scattering. Multiple wavelengths may be used to enhance selectivity.

Absorbance measurements that are sensitive to scattering or optical path length can be corrected by using known relationships between the refractive index and the scattering properties of the medium. For example, the empirical relationship between wavelength and scatter intensity may be used to estimate the extent of scatter at wavelengths where direct measurement of scatter are difficult. For example, polarimetric measurements described above can be performed in the visible region or NIR region and used to normalize the measurements made at other wavelengths, e. g. measurements in MIR region.

Corrections for pH, Electrolyte Concentrations, and Temperature

Vibrational spectroscopies are sensitive probes of molecular conformation. In the context of the present invention, the vibrational absorption bands in the NIR, MIR, and Raman spectra that result from the C—O and H—O—H stretching vibrations are particularly important. The vibrational frequencies and intensities of these bands depend upon the hydrogen bonding characteristics of the sample. In turn, hydrogen bonding is strongly dependent upon pH, electrolyte concentrations, and temperature. As a result, these parameters can cause variability in measurements involving vibrational modes that are sensitive to hydrogen bonding.

To some degree, vibrational spectra can be "self-corrected", that is, certain vibrational bands that arise from electrolytes can be used to correct for the impact of the electrolyte concentration on other bands (e. g. H-bonding bands). Other techniques may also be used to correct the vibrational spectra for electrolyte effects. For example, PAS spectra are sensitive to changes in electrolyte concentrations because electrolytes alter the speed of sound in the sample. Thus, a PAS measurement could be used to correct the IR absorbance measurements for the effects of electrolytes.

The temperature dependence of the MIR water spectrum complicates glucose measurements by providing a variable background signal that must be subtracted in order to reveal the glucose information. Raman scattering can be an accurate measure of temperature. The ratio of the intensities of corresponding Stokes and Anti-Stokes bands can be used to measure the temperature of a sample.

Spatial dimensions may also be used to sort out the contributions from pH, electrolytes, and temperature. A temperature gradient exists between the outer surface of the skin and the tissue inside. Accordingly, the effects of temperature on the measured signal should scale with the distance into the tissue (normal to the tissue surface) whereas contributions from electrolyte concentrations and pH should be more evenly distributed. Thus, in the foregoing example, a spatial dimension is used to separate out the effects of temperature on the measured signal from those effects due to pH and electrolyte concentrations.

Temporal dimensions provide additional selectivity which can be used to sort out the contributions from pH, electrolyte, and temperature changes. As shown in Table 2, oscillations in temperature and electrolyte concentrations have higher characteristic frequencies than those for pH. A measure of spectral changes as a function of time, therefore, allows the different variables to be selectively extracted, based upon a temporal dimension.

Corrections for Pulsatile Flow and Body Part Movement

Both MIR and NIR measurements are highly sensitive to body part movement, because the measurement is a function of the optical alignment and path length. The effect of pulsatile flow depends on the time constant of the measurement. For NIR or MIR measurements, where integration times are fairly short, pulsatile flow variability can be normalized by using integration times that are shorter than the pulse length. For measurements that require longer integration times, such as Raman, pulsatile flow effects can be averaged over multiple measurements.

Photoacoustic measurements are less sensitive to these variables because the measured signal is a function of optical and (mostly) acoustic coupling efficiencies. Because the measurement method for photoacoustics uses short laser pulses, photoacoustic measurements may be less sensitive to body part movement and pulsatile flow.

Corrections for Sample Heterogeneity

Figure 2:
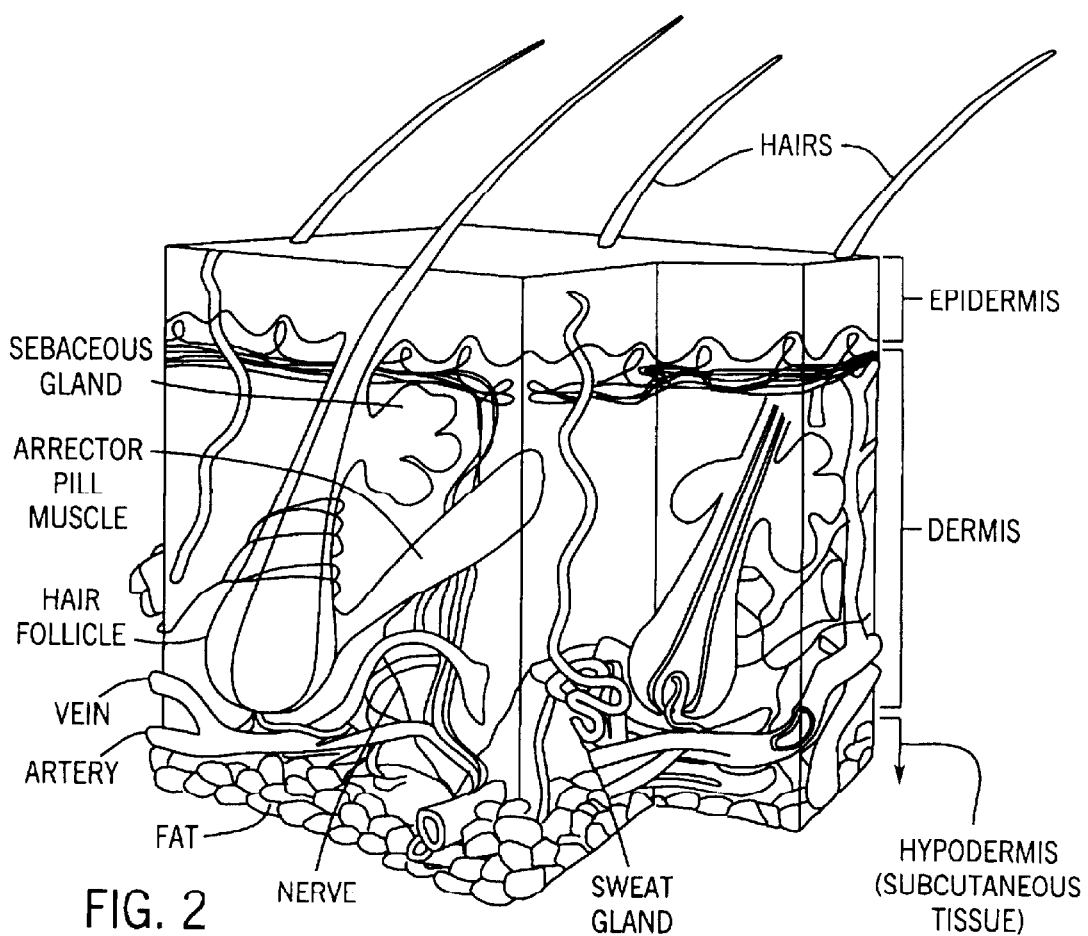
FIG. 2 is a schematic diagram of the skin.

For noninvasive measurements of in-vivo parameters, the incident radiation must pass through the stratum corneum before reaching viable tissues, and hence the thickness, composition, and morphology of the stratum corneum can affect measurements (see FIG. 2). As the beam penetrates into the tissue, the radiation may be scattered, absorbed, reflected or emitted by structures and chromophores that can vary dynamically and between individuals. As a result, the beam intensity decreases rapidly as it penetrates into the tissue and the majority of the spectroscopic signal arises near the surface of the tissue where the light intensity is at a maximum. As defined herein, the penetration depth, d, is the distance within the tissue at which the incident light intensity ($I_o$) falls to ($I_o/e$).

The scattering, absorption, and emission properties vary with the wavelength and the polarization state of the incident light. Light of different wavelengths may reach vastly different penetration depths within the tissue, and essentially all noninvasive measurements are dependent on wavelength and polarization. This effect can be used to advantage, since a judicious choice of wavelength and polarization state can provide a level of control over the depth to which the tissue will be probed by the radiation. This control can be used to selectively extract information related to particular chromophores, based on their predictable, or measurable, spatial locations within the sample.

Spatial dimensions can provide an additional level of selectivity for spectroscopic measurements in complex samples. In particular, it would be useful to measure blood glucose to the exclusion of glucose in the skin, and vice versa. Blood and interstitial fluid measurements may be the measurements of highest clinical utility; however, glucose concentration measurements in other regions of the tissue may also prove useful. Hypoglycohistiosis (the glucose decrement in tissue) sometimes precedes hypoglycemia. This characteristic could be measured as an early indicator of hypoglycemia.

Wavelengths in the MIR and FIR regions are suitable for measuring glucose in the skin. In this case, the blood constitutes a relatively small fraction of the tissue volume under spectrometric examination. MIR and FIR measurements of skin glucose concentrations can be subtracted from the NIR spectrometric assay, which probes both the skin and the underlying tissues and vasculature.

Spatial dimensions that are generally parallel to the skin surface can also be used to provide additional selectivity. Spectroscopic images of biological tissues generally contain regular repeating structures. Image analysis techniques (such as multidimensional Fourier transformation, segmentation, or some other image processing technique) can be used to extract signals contained in certain locations or spatial frequencies in the image.

For example, a spectroscopic image of a tissue sample may reveal blood vessels of regular sizes and separation distances. Such structures will contribute particular spatial frequencies to the image. Selective spectroscopic information may be obtained from these structures by collecting a spectroscopic image (i.e. recording a spectroscopic variable as a function of two spatial variables) and performing a multidimensional Fourier transform on the spectroscopic image. The signals resulting from the blood vessels would then be selectively obtained by measuring the spectroscopic signal intensity as a function of spatial frequency. An additional advantage of the foregoing method is that the measured signal is relatively insensitive to changes in alignment or sample positioning.

The following non-limiting examples will further illustrate this invention.

EXAMPLE 1

Figure 3:
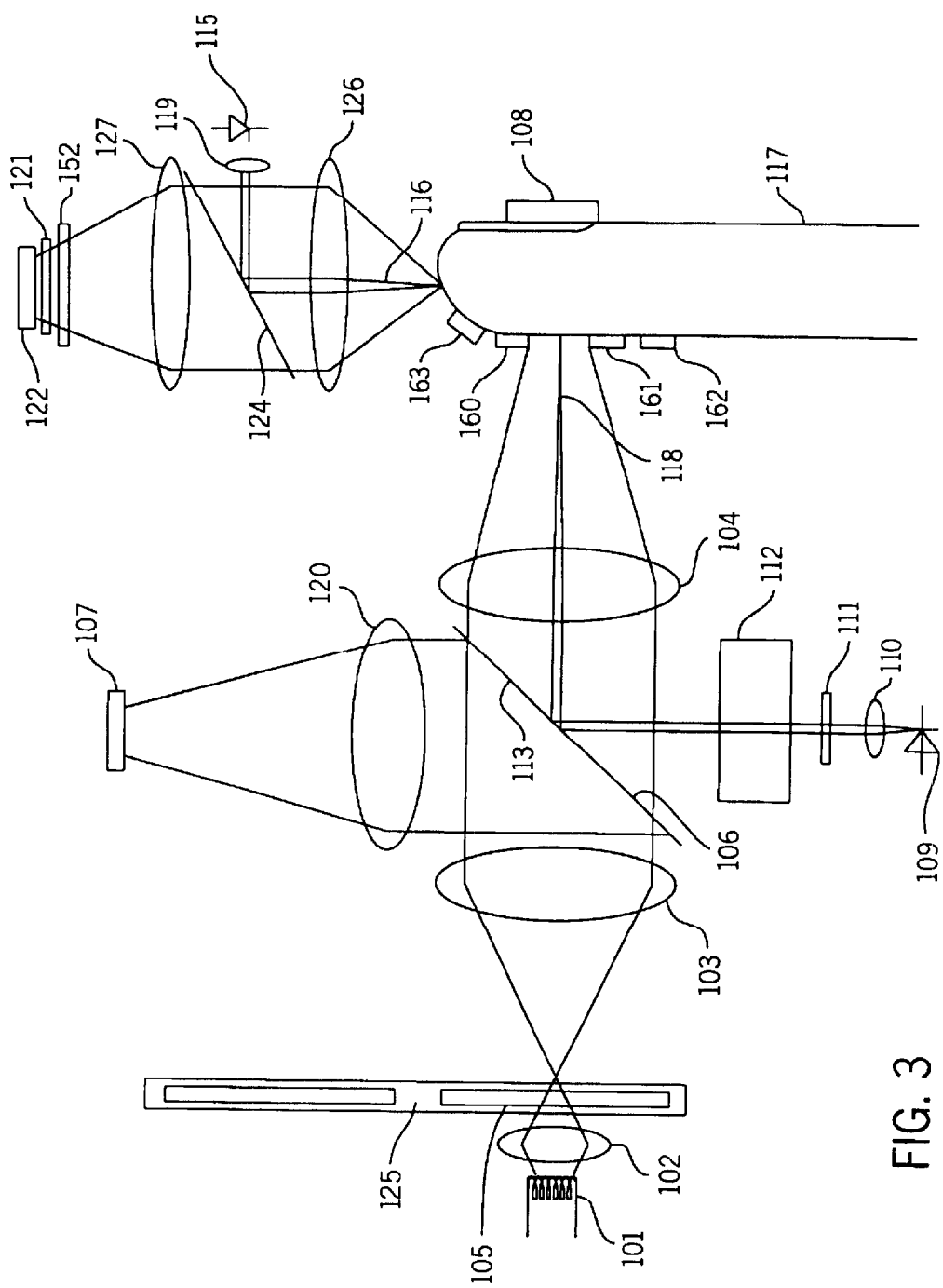
FIG. 3 is a schematic diagram of a multiplex sensor according to one embodiment of the present invention.

FIG. 3 is a schematic diagram of one embodiment of the present invention. The embodiment comprises a multiplex sensor for measuring one or more parameters in a sample, e. g. the glucose concentration in a finger.

IR light from a broadband IR light source 101 is focused by a lens 102 and passed through an optical filter 105 to produce a narrow band of light. Optical filter 105 can be any filter having a predefined wavelength of maximum transmission ($\lambda_{max}$) and a predefined spectral bandpass ($\Delta v_{1/2}$). For example, optical filter 105 might consist of a dielectric filter, a holographic filter, or a thin polymeric film. Optical filter 105 may be secured in a fixed holder or, alternatively, it may be held in a filter wheel 125 that may contains other optical filters having different values of $\lambda_{max}$ or $\Delta v_{1/2}$. In operation, filter wheel 125 can be rotated to provide one or more filters in the optical path having predefined optical properties, such as a preselected $\lambda_{max}$ or $\Delta v_{1/2}$.

The filtered light-is focused onto a body part, e. g. a finger 117, by a focusing means comprising, for example, lenses 103 and 104. While a finger has been used in the present example, it should be understood that other body parts, such as the earlobe, may be preferred, depending upon the measurement to be made and the physical characteristics of the body part. Lenses 102, 103, and 104 are, preferably, achromatic over the wavelength ranges used for the measurement. It should be understood that alternative means for providing focused light may be substituted for lenses 102, 103, and 104. Such focusing means might comprise, for example, reflective optics such as a parabolic mirror, a Cassegrain mirror, or the like. Reflective optics have the advantage of being less susceptible to chromatic aberrations, particularly in the infrared region.

Lenses 102, 103, and 104 may be held in a fixed position or, alternatively, may be moved in order to alter the focal point within the tissue or at the tissue surface. Such an altered focal point might comprise, for example, a focal point that is translated along an axis normal to the skin surface or in a direction parallel to the skin surface. For example, such a moving focal point of light might be used to make measurements as a function of the spatial position of the focused light beam. Alternatively, a defocused beam of light may be used to minimize the power density at the tissue surface or for imaging applications where it is desirable to distribute light evenly across the tissue sample.

Detector 108, which is typically disposed on the opposite side of the Is finger from source 101, measures the intensity of the IR light that is transmitted through the finger. In operation, detector 108 may be used to measure the light intensity at one or a plurality of different wavelengths.

The determination of one or several parameters of interest (e. g. the concentration of various analytes such as glucose) may be made by comparing the transmitted intensity to a calibration standard for the parameter of interest or by comparison to a physical model of the sample under examination. Wavelengths in the range of 600–3000 nm may be selected.

A reflective or partially reflective optical element, such as a neutral density filter 106, diverts a small fraction of the filtered light from source 101 through lens 120, which focuses the light onto a reference detector 107. The reference detector provides a signal that is proportional to the light intensity incident on the finger and can be used to normalize the measured transmittance signals with respect to fluctuations in the intensity of the light from source 101.

For photoacoustic measurements, light from a light source 115, preferably a diode laser, is collimated by a lens 119 and reflected by a reflective element 124, such as a dichroic beamsplitter. It should be understood that alternative reflective elements, such as a holographic filter, may also be used. In operation, reflective element 124 is predominantly reflective for the excitation wavelength and predominantly transmissive at other wavelengths. For example, a dichroic beamsplitter that is 90% reflective at the wavelength emitted by light source 115 and 90% transmissive for longer wavelengths may be used.

Returning to FIG. 3, the light that is reflected by reflective element 124 is focused by lens 126 onto the finger 117. Lenses 126 and 127 are preferably achromatic over the wavelength ranges employed for excitation. A photoacoustic (PA) detector 163 is disposed adjacent to the finger 117. In a preferred embodiment, the PA detector 163 is in contact with the finger. In a particularly preferred embodiment, the PA detector 116 is held against the finger by an external force provided by, for example, a spring, a clip, or an inflatable cuff (not shown).

Light source 115 is switched on and off (pulsed) repetitively, preferably at a frequency of between about 0.1–10 kHz. Detector 163 generates an electrical signal in response to the applied acoustic wave. Detectors such as a piezoelectric transducer made of a material such as lead metaniobate, lead zirconate titanate, or polyvinylidene fluoride may be used.

A material that improves acoustic coupling between the finger and the acoustic detector may be used to enhance sensitivity. Such coupling materials act to reduce the acoustic impedance mismatch between the detector and the sample and may include a polymer or a gel that is both non-toxic and capable of providing enhanced coupling efficiency.

An important point regarding the present invention is that it does not rely upon a knowledge of the "degree of absorption" of the sample. Analyte concentrations may be determined directly by comparison to a calibration curve that relates the acoustic signal intensity to the analyte concentration.

Normalization of the acoustic signal may be accomplished by a number of alternative means. For example, the measured photoacoustic signal may be normalized to the intensity of the light emitted by light source 115. Alternatively, a measurement of the scattered intensity may be made at detector 122 (as described below).

Although a single light source is shown for this example, it should be understood that multiple monochromatic light sources could be substituted for light source 115 without departing from the spirit of the present invention. Multiple light sources could also be multiplexed to provide a measurement with higher throughput, thereby increasing the signal to noise ratio.

Figure 4:
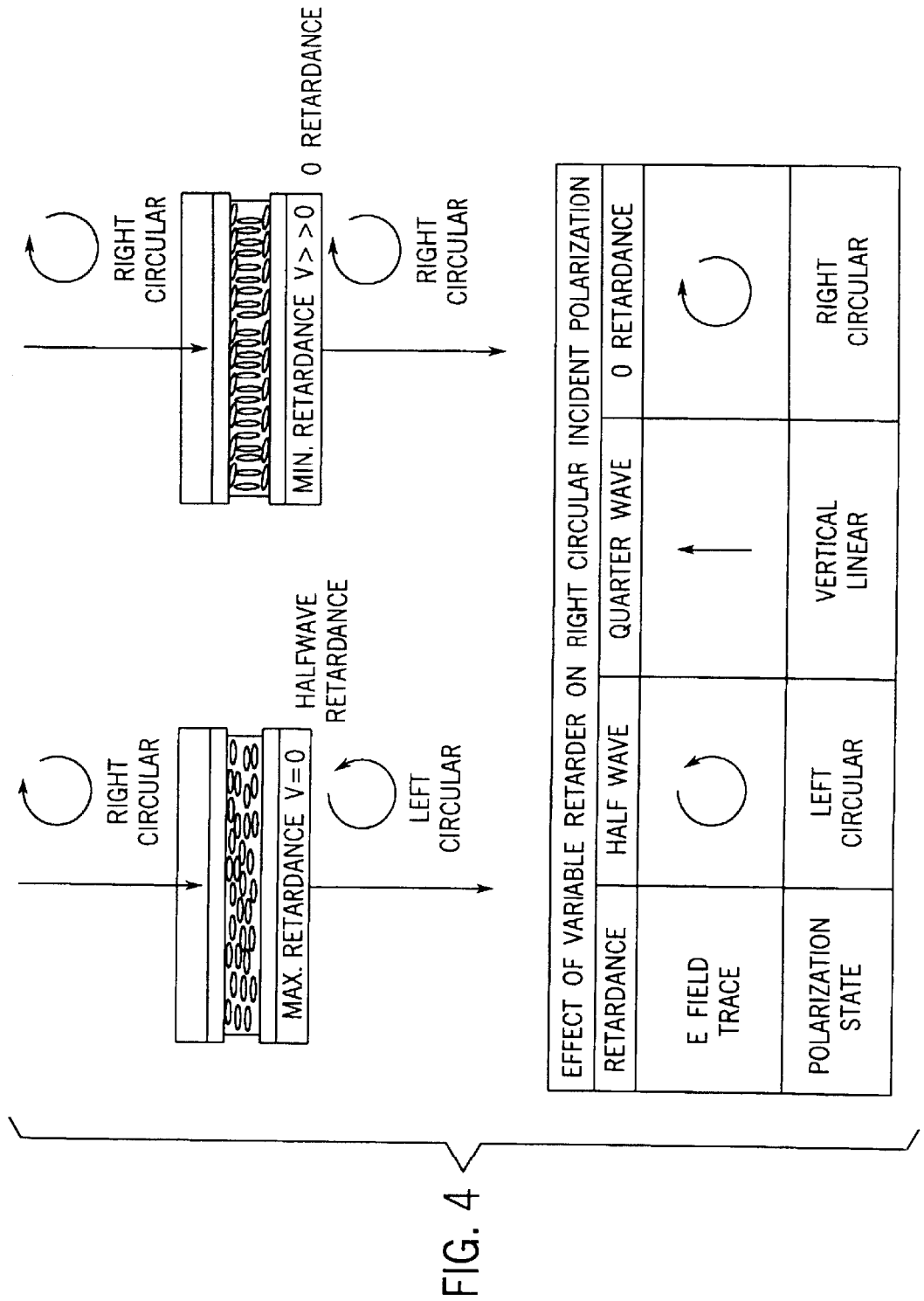
FIG. 4 is a depiction of the polarization states produced when a beam of right circular polarization state is transmitted through a half wave variable retarder. A liquid crystal polarization modulator is shown, but other polarization modulators can also be used.
Figure 5A:
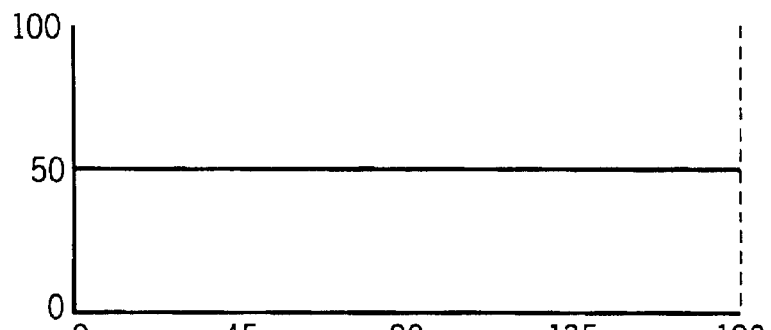
FIG. 5 is a depiction of the scattered light intensity predicted for a sample which interacts with the light produced by the polarization modulator of FIG. 4, wherein the sample behaves as: (a) a linear polarizer oriented at 45°, (b) a linear polarizer oriented at 0°, and (c) a circular polarizer.
Figure 5B:
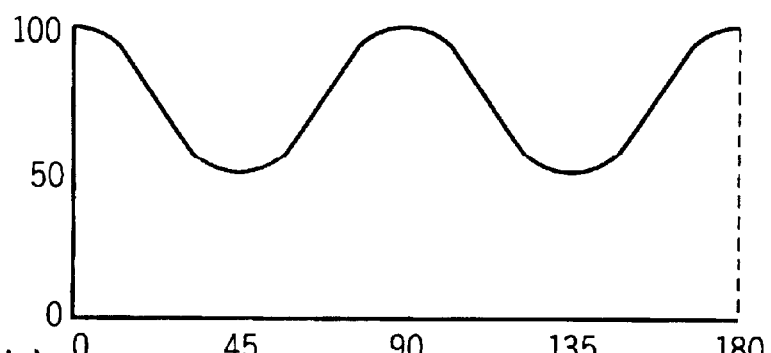
Figure 5C:
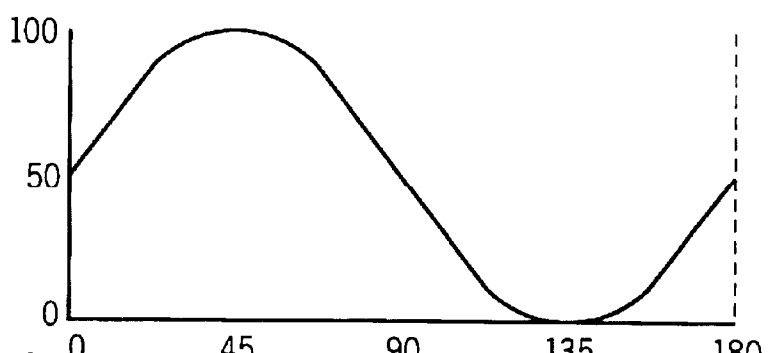

As shown in FIG. 3, light from a light source 109, preferably a diode laser, is collimated by lens 110 and passes through a circular polarizer 111 and a polarization modulator 112, which produces a series of polarization states over time. In one embodiment, the polarization modulator comprises a liquid crystal variable retarder, which provides a polarization state series consisting of right circular, vertical, left circular, vertical and so on (as shown in FIG. 4), where the numbers shown indicate the angle of rotation of the linear retarder. It should be understood that a variety of polarization state modulators can be used with the present invention including, for example, photoelastic modulators, electrooptic modulators, liquid crystals, magnetooptic modulators, and linear retarders.

Referring again to FIG. 3, the light exiting the polarization modulator is reflected from a patterned mirror 113 and focused onto the finger. The purpose of this beam is to measure the depolarization and diattenuation of the finger (or other body part, such as an earlobe). Measurements of the intensity of the scattered light are made by the detectors 160, 161, and 162, which are placed close to or, preferably, in contact with the finger 117. A circular polarizer is placed immediately before the active area of each detector. The circular polarizer transmits right-circular polarized light and blocks left-circular polarized light. As defined herein, close to the skin means within about 0 to 10 mm from the surface of the skin, preferably from about 0 to 1 mm from the surface of the skin or, most preferably, in contact with the skin. The placement of detectors 160, 161, and 162 close to or, preferably, in contact with the skin provides several advantages including:

(1) the capability of resolving small angular and spatial distributions of the scattered light, (2) forming an optical seal between the detector and the skin, thereby rejecting ambient light, and (3) optimizing collection efficiency, thereby increasing the signal to noise ratio.

As shown in FIG. 3, three detectors 160, 161, and 162 are used to detect the backscattered radiation; however, it is to be understood that a different number of detectors can be used. Detectors 160, 161, and 162 generate electrical signals that are representative of the intensity and polarization state of the scattered radiation. These electrical signals can be analyzed by means of a lock-in amplifier that is tuned to the modulation frequency of the polarization modulator or harmonics of that modulation frequency. Alternatively, the electrical signals produced by the detectors 160, 161, and 162 can be digitized and analyzed by means of a digital filter, such as a Fourier Transform.

FIG. 4 shows the polarization states generated by a liquid crystal variable retarder. The figure shows a schematic of a common liquid crystal modulator, an aligned nematic liquid crystal modulator. The three essential features of the nematic liquid crystal material are that (1) on average, their long axes align with respect to one another, (2) they display birefringence aligned with their long axes, (3) an electric field will cause them to tilt in the direction of the electric field. With no voltage applied, the liquid crystal molecules lie parallel to the glass substrates and maximum retardance is achieved. When a voltage is applied, the molecules begin to 'tip' perpendicular to the windows. As the voltage increases, molecules tip further, thereby causing a reduction in the effective retardance. The figure shows the two conditions for half wave retardance and zero retardance, and the resulting polarization states. The transition between half wave and zero retardance is smooth, allowing a smooth transition of left circular to linear to right circular.

If the sample is non-polarizing, then the modulation at the detector will be a sinusoid at the modulation frequency of the polarization modulator. As the depolarization of the sample increases, the frequency of modulation does not change, but the amplitude of the modulation does. The amplitude of the modulation is proportional to the amount of depolarization in the sample. The linear diattenuation is proportional to a frequency that is two times the modulation frequency of the modulator.

Polarization measurements may also be carried out at multiple wavelengths to enhance selectivity. Any wavelength between 400 nm and 12 microns may be used. Returning again to FIG. 3, a preferred embodiment employs polarization measurements that are normalized to the intensity of incident light by recording the light that is transmitted through patterned mirror 113 and focused onto detector 107. The intensity of light at the finger 117 can be derived by reference to a calibration performed at the factory. The polarization measurements described above may be related to the concentration of at least one analyte in the sample by comparison to a calibration curve.

Returning again to FIG. 3, the present invention provides a means for performing Raman and emission measurements as follows. Light from a light source 115, preferably a laser, is collimated by lens 119 and reflected by a dichroic beamsplitter 124. The reflected light is focused by lens 126 and impinges on the finger 117. At least one of Raman scattering, fluorescence, or phosphorescence is collected and collimated by lens 126 and focused by lens 127 onto a wavelength selective element 121. Lens 127 is preferably optimized to concentrate the incident light beam onto detector 107 and to match the geometrical characteristics of the collected light to the size and acceptance angle of the wavelength-selective element 121 and the detector 122. In a preferred embodiment, a Rayleigh rejection filter 152 is inserted in the optical path between lens 127 and wavelength-selective element 121. Rayleigh rejection filter 152 may comprise, for example, a holographic filter, a dispersive element combined with a spatial filter, a dielectric filter, an electronically tunable filter such as an acousto-optic tunable filter (AOTF) or a liquid-crystal tunable filter (LCTF), or any other filter having suitable Rayleigh rejection characteristics. In a preferred embodiment, Rayleigh rejection filter 152 comprises a holographic filter.

Wavelength-selective element 121 allows certain wavelengths of light to be transmitted to the detector 122 by means of either a dispersive or interferometric selection mechanism. Wavelength selective elements, such as a Czerny-Turner monochromator, can be used in a scanning mode with a point detector or, preferably, the wavelength selective element is coupled to an array detector. A typical array detector may be a silicon photodiode array or, in a preferred embodiment, the array detector may be a charge coupled device (CCD) or Charge Injection Device (CID) detector. InGaAs detectors are optimized for the NIR and can be operated at room temperature or cooled to liquid nitrogen temperatures.

Wavelength selective element 121 may alternatively comprise a dielectric or holographic filter or a tunable filter such as AOTF or a LCTF. An advantage of such tunable filters is that they contain no moving parts and can be rapidly tuned to one or a plurality of different wavelengths. With the injection of a combination of radio-frequency signals into its transducer, the AOTF can act as an electronically controllable, multiplexing spectrometer. If used in multi-wavelength mode, multiple wavelengths can be measured essentially simultaneously.

EXAMPLE 2

Figure 6:
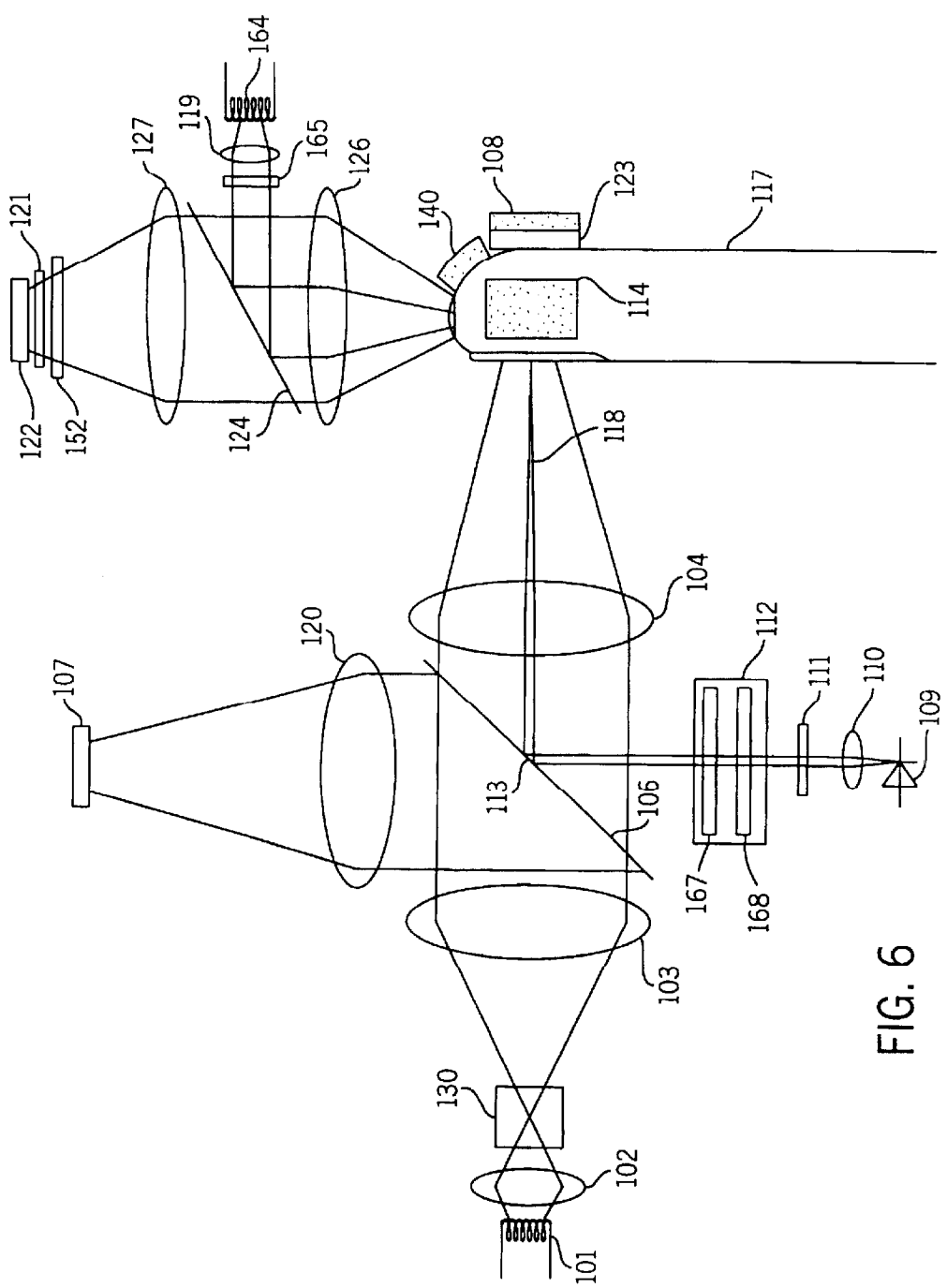
FIG. 6 is a schematic diagram of a multiplex sensor according to one embodiment of the present invention.

FIG. 6 shows an alternative embodiment of the multiplex sensor shown in FIG. 3. Elements having the same reference numerals in FIG. 6 have the same identities and descriptions as in FIG. 3. The embodiment shown in FIG. 6 comprises several additional elements.

Infrared Absorbance

Optical filter 130 comprises a tunable optical filter, such as an AOTF, a LCTF, or any other filter that is tunable and allows for the passage of one or more narrow bands of light. Multiple light pulses having different wavelengths may be transmitted consecutively over time or, alternatively, may be transmitted essentially simultaneously. Detector 108 measures the transmitted IR light at one or a plurality of different wavelengths. A multiplexing algorithm may be used in combination with filter 130 and detector 108 in order to measure the transmitted intensity at several wavelengths.

As shown in FIG. 6, the combination of a broadband light source with a tunable optical filter 130, produces one or more narrow bands of radiation having selected wavelengths. It should be understood that an equivalent means for providing broadband light can be substituted without departing from the spirit of the present invention. For example, one equivalent substitute would comprise the combination of several monochromatic light sources into one beam as shown in FIG. 7.

Figure 7:
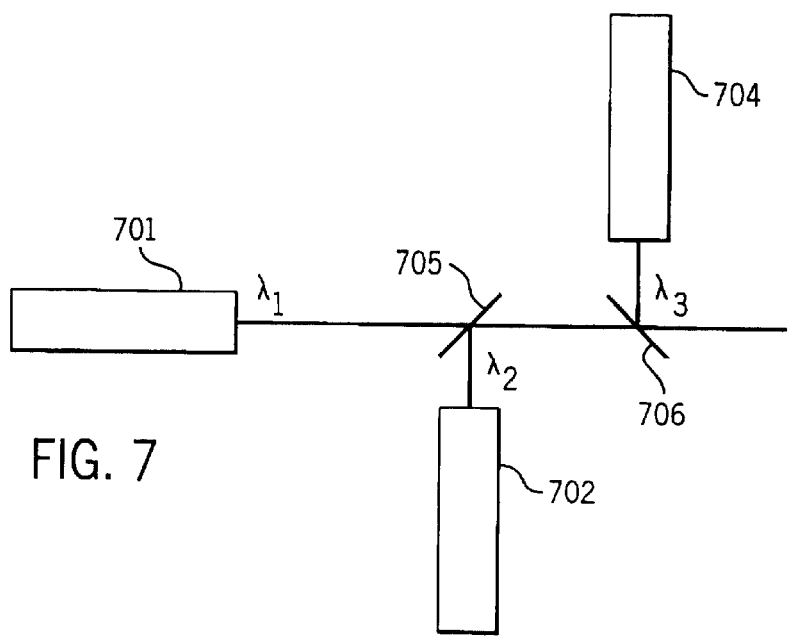
FIG. 7 illustrates the combination of several monochromatic light sources into one polychromatic light source.

FIG. 7 shows a combination of three light sources 701, 702, and 703 having different wavelengths $\lambda_1$, $\lambda_2$, and $\lambda_3$. Light emitted from light sources 701 and 702 is incident upon dichroic beamsplitter 705, which transmits most of the light at wavelength $\lambda_1$ and reflects most of the light at wavelength $\lambda_2$. As a result, a polychromatic beam of light having a components at two different wavelengths, namely $\lambda_1$ and $\lambda_2$, is produced. This combined beam then impinges upon dichroic beamsplitter 706, which transmits light at wavelengths $\lambda_1$ and $\lambda_2$ and reflects light at $\lambda_3$. In principle, this method could be used to combine as many light sources as needed for the measurement. Other means for combining multiple monochromatic light beams are well known in the art and may also be substituted for the broadband light source 101 in the present invention. Infrared light at one or more different wavelengths may be transmitted consecutively over time or may be transmitted essentially simultaneously.

Returning again to FIG. 6, polarization modulator 112 comprises two variable retarders 168 and 167. Linear polarizer 111 is oriented at 0°, thereby defining a global coordinate system, and is followed by a first variable retarder 168, e. g., a liquid crystal modulator, an electro-optic modulator or some other variable retarder, with its fast axis oriented at 45° relative to the linear polarizer. The first variable retarder is followed by a second variable retarder 167 with its fast axis oriented parallel to the transmission axis of the polarizer.

One advantage of the polarization modulator shown in FIG. 6 is that it does not require mechanically moving parts that can introduce vibrational noise into the measurement. Additionally, it can achieve modulation frequencies that are higher than the characteristic frequencies of physiological variables. Another advantage of these modulators is that they are inexpensive to manufacture in mass quantities.

As shown in FIG. 6, a single detector 114 measures the intensity of the scattered radiation as a function of the incident polarization state. Detector 114 may comprise a point detector or an imaging detector, such as a CCD, a CID. In a preferred embodiment, detector 114 is a point detector. A point detector, such as a photodiode, has a faster response time than the CCD and, therefore, is more amenable to high frequency modulation and detection schemes. In an alternative embodiment, the scattered light is measured using an imaging detector, such as a CCD or a CID. An imaging detector has the capability of recording the scattered intensity as a function of one or more spatial dimensions along the skin surface.

As will be described more fully below, some polarization measurements (e. g. depolarization) require the placement of a polarization state analyzer 123 between the finger and the detector 114. Typical polarization state analyzers may include a photo-elastic modulator followed by a linear polarizer, a liquid crystal variable retarder followed by a linear retarder, an electro-optic crystal followed by a linear retarder or a polarizer.

In a preferred embodiment, polarization state analyzer 123 is a simple thin film polarizer, such as a stretched polymeric film, positioned in front of the detector 108. The polarizer may be either a linear polarizer or a circular polarizer. In a particularly preferred configuration, depolarization is measured by modulating the incident polarization state as shown in FIG. 4, and analyzing the scattered light with a fixed polarizer.

Although a finger is shown in FIG. 6, it should be understood that other body parts, such as an earlobe, may be preferably used for depolarization measurements in order to increase the sensitivity of the measurement. For example, the internal structures (bones, cartilage, tendons) of the finger will almost completely depolarize the light which is incident on the finger. The polarization state of light passing through the earlobe, however, is preserved to a greater degree due to the lower amount of internal structure in the earlobe relative to the finger.

Light source 164 is a broadband light source or a combination of several narrow band sources (as described above and in FIG. 7). A tunable optical filter 165, such as an AOTF as described above, is used to select one or more wavelengths of light for photoexcitation of the sample.

The acoustic detector may be optimized to enhance coupling efficiency in a number of ways. For example, the surface of PA detector 140 is curved to match the contour of the body part with which it interfaces. For example, the detector could be conically, hemispherically, or parabolically shaped to provide maximum coupling efficiency. The detector could also be a semi-cylinder or comprise any other geometrical shape that maximizes the sensitivity or selectivity for the measured analyte. In a preferred embodiment, the PA detector is hemispherically or semi-cylindrically shaped to match the contour of the body part.

EXAMPLE 3

Figure 8:
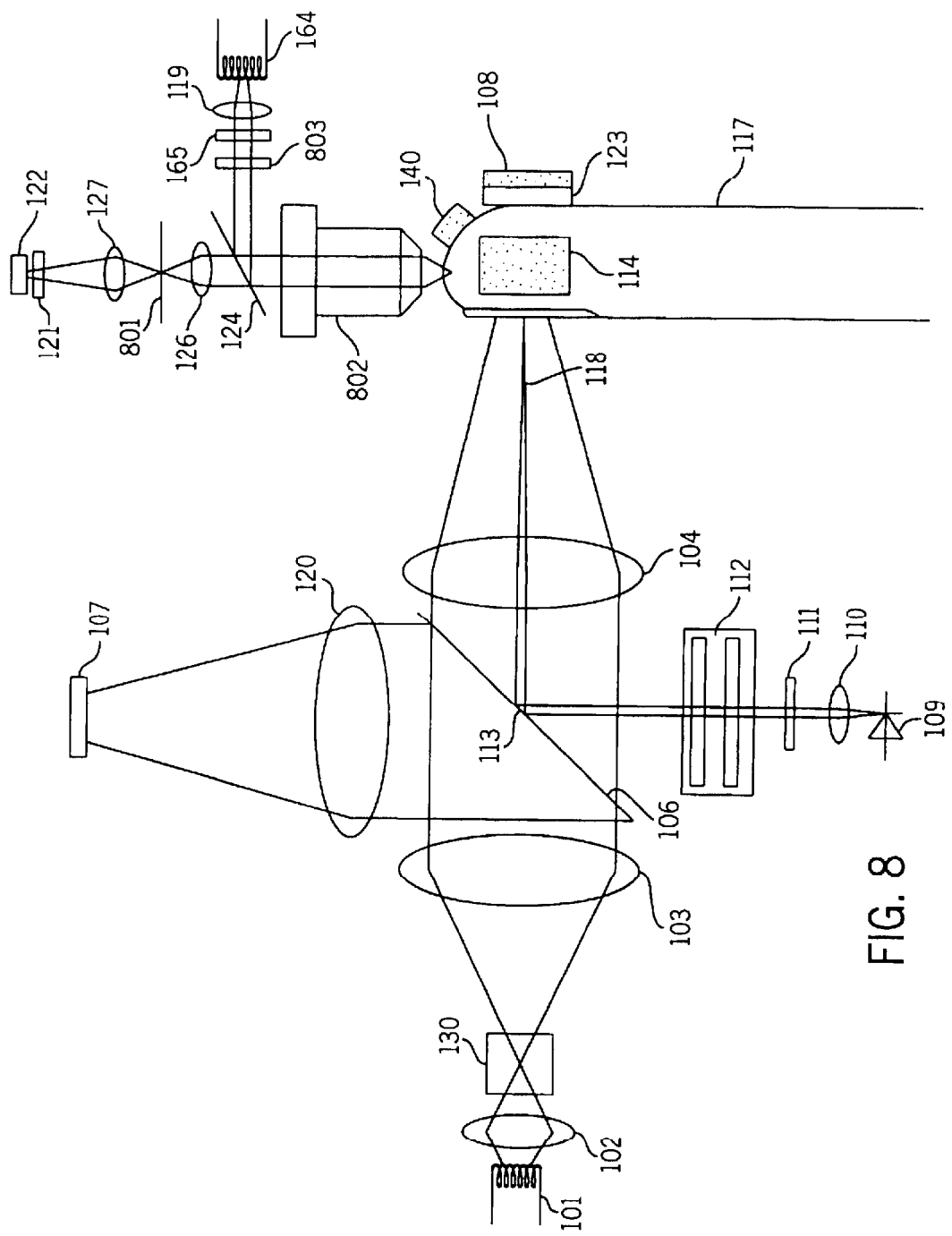
FIG. 8 is a schematic diagram of a multiplex sensor according to one embodiment of the present invention.

FIG. 8 shows an alternative embodiment of the multiplex sensor shown in FIG. 3. Elements having the same reference numerals in FIG. 8 have the same identities and descriptions as in FIG. 3. The embodiment shown in FIG. 8 comprises several additional elements.

The apparatus of FIG. 8 comprises a multispectral imaging system that uses multiple spectral dimensions (i.e. IR, Raman, Fluorescence, etc.) and one or more spatial dimensions. Additionally, a series of measurements may be performed over time, thereby adding a temporal dimension.

Light from broadband light source 164 is collimated by lens 119 and passes through optical filter 165 and polarization modulator 803 before being reflected by reflective element 124. Light that is reflected by reflective element 124 passes through a focusing means, such as microscope objective 802. Microscope objective 802 is preferably corrected to provide a flat image field and is achromatic.

The system shown in FIG. 8 exhibits several advantage. First, multiple spectroscopic images may be recorded. The system shown in FIG. 8 might, for example, be used to measure a temporal oscillation in one or more parameters of the sample.

By using imaging detectors and image analysis techniques, such as a multidimensional Fourier transform, the signals that are contained in particular spatial frequencies across an image plane of the tissue sample may be selected. For example, a spectroscopic image of a tissue sample will contain blood vessels of regular sizes and such structures will contribute particular spatial frequencies to the image. Spectroscopic information may be obtained from these structures by collecting a spectroscopic image (i. e., an image at multiple wavelengths) and performing a multidimensional Fourier transform on the spectroscopic image. Other image processing techniques, such as segmentation, may also be employed.

The systems described in FIG. 8 can be used in conjunction with a pattern recognition algorithm to determine if the noninvasive instrument is in the appropriate position for making a measurement. Positioning could be adjusted as part of a calibration routine or, alternatively, could be a monitored as a function of the signal intensity produced by one or more parameters of the sample. Such a system could be coupled to an alarm to warn the patient when the sensor is not positioned properly. Optimally, the alarm may include a directional indicator, which would allow the patient to move the sensor to the proper position for measurement.

EXAMPLE 4

Figure 9:
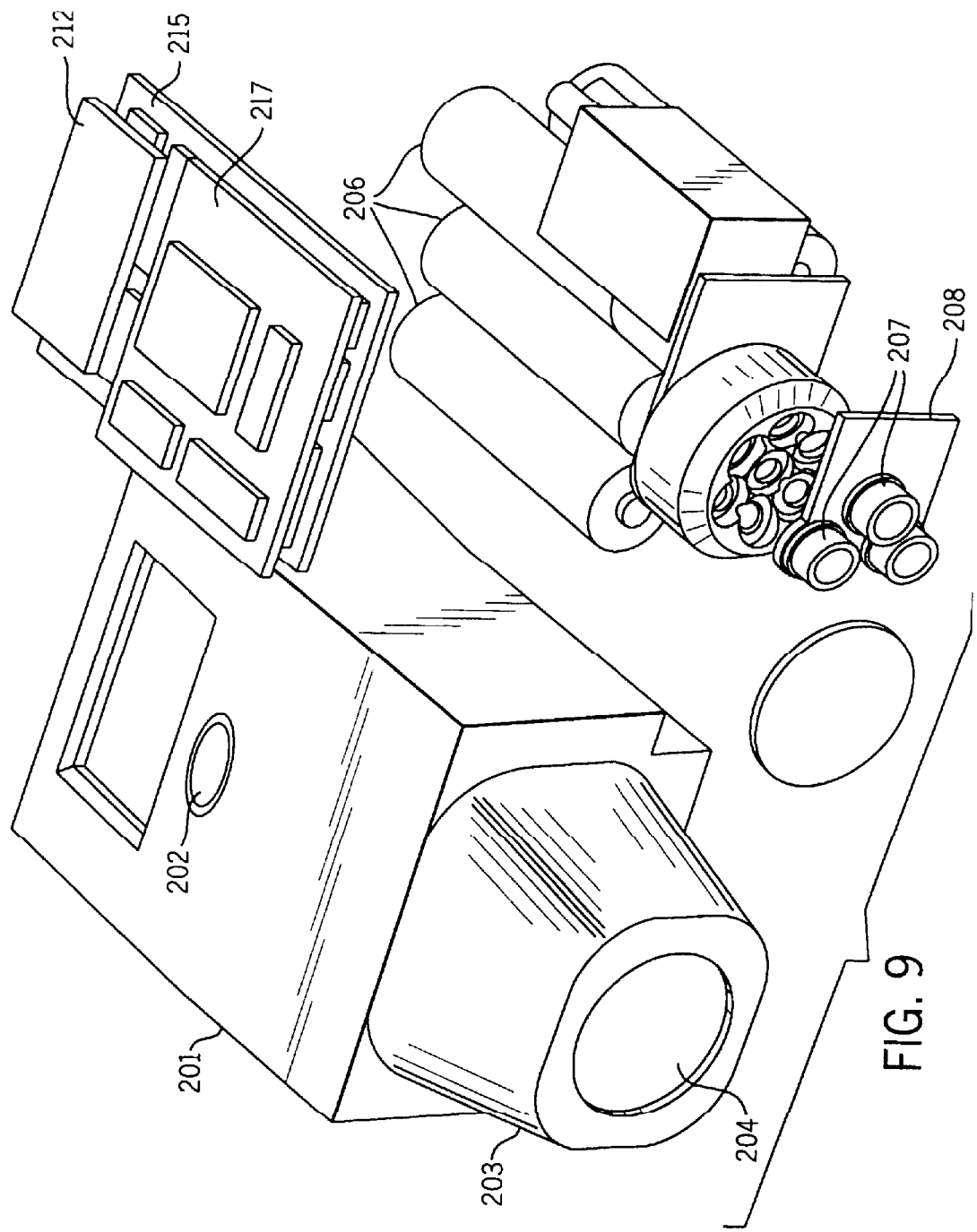
FIG. 9 is a schematic diagram of a multiplex sensor according to one embodiment of the present invention.

An exploded view of another embodiment of the present invention is provided in FIG. 9. Device 201 is a hand-held, noninvasive multiplex sensor that may be used for measuring at least one parameter (e. g. the concentration of an analyte such as glucose), in a sample, (e. g. a body part). An activating button 202 is depressed by the user to activate the instrument prior to Use. Optical head 203 contains an array of light sources and detectors and an optical window 204, which is transparent to the light that is emitted or detected by device 201. Appropriate light sources may be, for example, infrared emitting diodes (IREDs) or laser diodes. Photodetectors 207, which are also provided inside the optical head, measure the light that is backscattered by the sample. Preferred photodetectors may be, for example, a photodiode, a charge coupled device, or a charge injection device. Any other suitable detector may be used. The detectors are preferably optimized for a given wavelength range and may consist of, for example, silicon, InGaAs, Ge, or PbS detectors. Photodetectors 207 are attached to a preamplifier board 208, which contains electronic circuitry in accordance with its function. Batteries 206 provide power for the device. Optical window 204 could also be designed to filter out stray ambient light, thereby further reducing noise in the measurement.

Several preselected wavelengths of infrared radiation are focused onto the sample. Radiation that is reflected, emitted or scattered by the sample is collected by detectors 207. Quantitative analysis is performed by the central processing unit 215 in conjunction with a multivariate calibration model and algorithms stored in module 217. A concentration value is subsequently displayed by a display unit 212, which is connected to the central processing unit 215. Display unit 212 is preferably a liquid crystal display, which is large enough to be easily read by patients with visual dysfunction, such as that caused by advanced stage diabetes. Alternatively, an audible readout may be provided.

EXAMPLE 5

One embodiment of the present invention provides a method of measuring in-vivo glucose concentrations that combines measurements of infrared absorbance (in both forward and backscattering geometries) with diattenuation measurements. The results of these measurements are shown in Table 3 below.

TABLE 3

| Measurement | Wavelength (nm) | % CV |
| --- | --- | --- |
| 1. IR, Forward Scattering | 1000 nm | 26.1 |
| 2. IR, Forward Scattering | 1150 nm | 25.9 |
| 3. IR, Backscattering | 1400 nm | 23.8 |
| 4. IR, Backscattering | 1650 nm | 23.1 |
| 5. DC scatter | 633 nm | 26.2 |
| 6. Circular diattenuation | 633 nm | 25.6 |
| 7. 1–4 combined | | 17.2 |
| 8. 1–6 combined | | 16.5 |

The precision of the combined IR absorbance measurements is described by a coefficient of variation (% CV) of 17.2. As shown in Table 3, the measurement precision is improved (% CV=16.5) by combining the diattenuation measurements with the IR absorbance data.

EXAMPLE 6

Another embodiment of the present invention provides a method of measuring blood glucose that is corrected for spectral variables (such as water (tissue hydration), hemoglobin, tissue scattering (refractive index), and temperature) by means of a combination of complementary spectroscopic techniques. Specifically, glucose measurements are performed using a combination of infrared absorbance, photoacoustics, and scattering measurements.

EXAMPLE 7

Another embodiment of the present invention involves a method of measuring the concentration of at least two analytes as a function of at least two spectral dimensions, one spatial dimension, and one temporal dimension.

A sample is illuminated with infrared light and the infrared absorbance is measured as a function of the wavelength of light absorbed. A plot of the infrared absorbance versus wavelength is referred to as an infrared absorbance spectrum and has an associated spectral dimension, namely, the wavelength of the light absorbed by the sample. Within the same embodiment, at least one additional complementary spectroscopic technique is applied, (e. g. Raman scattering, photoacoustics, polarimetry, fluorescence spectroscopy, etc.), thereby adding at least one more spectral dimension to the measurement.

Further, and within the same embodiment, at least two spectral dimensions are recorded as a function of at least one spatial dimension of the sample. In the present example, a spatial dimension of the sample may be measured using an imaging detector, such as a charge-coupled device (CCD) detector, or by multiple discrete detectors. Further, and still within the same embodiment, the measurements described above are performed over time in order to measure a temporal dimension. The concentration of the at least two sample constituents are thus measured as a function of at least two spectral dimensions, at least one spatial dimension, and at least one temporal dimension.

Recording the interactions of the incident light with the sample over multiple dimensions enhances the selectivity for the parameter(s) of interest by allowing for the separation, identification, and quantification of multiple contributors to the spectroscopic signal. Physiological and spectral interferences may be removed by virtue of their predictable or measurable contributions in any of the spectral, temporal, or spatial dimensions.

Various modifications and alterations of this invention will become apparent to those skilled in the art without departing from the scope and spirit of this invention. It should be understood that this invention is not to be unduly limited to the illustrative embodiments set forth herein but, rather, by the scope of the appended claims.

For example, while in-vivo glucose measurement has been the target of the current work, other measurements, in-vivo or in-vitro, needing improved specificity could benefit from measurements with combined technologies (i., e., alcohol, blood urea nitrogen (BUN), bilirubin, hemoglobin, creatine, electrolytes, blood gases, and cholesterol). It should be recognized that the wavelengths used for measurement will vary for the different analytes of interest. For biological samples, blood is the most frequently sampled fluid for observing the physio-pathological state of the patient. However, other body fluids such as interstitial fluid (ISF), cerebrospinal fluid (CSF), plasma, urine, aqueous humor, saliva, and sweat may also be used with the present invention. In addition, multiple spectroscopic measurements may be performed on the same body part or, alternatively, different body parts may be employed where there is an advantage due to engineering design, spectroscopic signal intensity, or patient compatibility.

A variety of wavelengths of light may be used without departing from the spirit of the present invention. Ideally, the wavelengths should be selected according to standard experimental optimization techniques. Such optimization techniques might include, for example, principal components analysis or genetic algorithms. The optimization algorithms may be applied to calibration solutions, tissue phantoms, or in-vivo measurements. Variations in some or all of the measured physiological or spectral variables may be measured independently by means of invasive or minimally invasive techniques. For optimizations performed in-vivo, the protocol may include the administration of oral glucose combined with subsequent measurements of glucose concentrations in the specimen.

A variety of detectors may be employed in the present invention without departing from the spirit of the invention. Preferably, the detectors should be optimized for the particular measurement to be made, with wavelength, cost, performance, and engineering design being considered. The detectors may be either single element or array detectors. While single element detectors are generally less costly and more amenable to frequency modulation and detection schemes, an alternative embodiment could use detector arrays, such as a photodiode array or a charge-coupled device (CCD) array, for multi-wavelength detection.

When performing multiple measurements, it is important to optimize the sensitivity of each detector while minimizing crosstalk with the other detectors. To that end, various filters and the like that transmit only the wavelength(s) of interest may be placed in front of the detectors. Such filters may include, for example, dielectric filters, holographic filters, and tunable filters, such as an Acousto-Optic Tunable Filter (AOTF). Alternatively, frequency modulation may be used to distinguish the measured signals of one spectroscopic technique from another.

The development of detectors having sensitivities extending continuously from visible wavelengths into the infrared will permit the use of a single detector, or detector array without the need to switch detectors. Where convenient, optical fibers may be used to deliver and collect light from the body part. Optical fibers have the advantages of lower cost, ease of manipulation in clinical settings, and possible endoscopic applications.

For practical use, the measurement device should be convenient and easily operable by a person with no particular skill in the physical sciences. The overall size of the device should be comparable to commercially available invasive glucose monitoring devices, i. e. small enough to be readily held in the hand of the user. It should not require power densities that will cause harm to the patient, and it should be economical to purchase and operate.

For noninvasive measurements on a body part, an insert may be adapted to change the shape of the body part or to change the physical relationship between the transducers and the body part. For example, the insert might be adapted to increase the pressure applied to the body part by the transducer. Such a change might be made, for example, to alter the acoustic coupling efficiency between the skin and the detector. The sampling rate of any of the above listed spectroscopic variables may be adjusted to correlate with oscillations in any of the physiological variables of the sample.

What is claimed is:

1. A method of determining the concentration of at least one analyte in a sample comprising the steps of:

(a) illuminating said sample with light;

(b) measuring at least one of diattenuation or polarization;

(c) relating the measurement of step (b) to the concentration of said at least one analyte, wherein said at least one analyte is hemoglobin.

2. The method of claim 1, wherein said at least one analyte comprises glucose.

* * * * *